US007267993B2

(12) United States Patent
Pentrenko et al.

(10) Patent No.: US 7,267,993 B2
(45) Date of Patent: Sep. 11, 2007

(54) PHAGE LIGAND SENSOR DEVICES AND USES THEREOF

(75) Inventors: Valery A. Pentrenko, Auburn, AL (US); Vitaly J. Vodyanoy, Auburn, AL (US); Alexandre M. Samoylov, Auburn, AL (US); Iryna Sorokulova, Auburn, AL (US); Viswaprakash Nanduri, Auburn, AL (US); Bryan A. Chin, Auburn, AL (US); James M. Barbaree, Dadeville, AL (US); W. Charles Neely, Auburn, AL (US)

(73) Assignee: Auburn University, Auburn, AL (US)

( * ) Notice: Subject to any disclaimer, the term of this patent is extended or adjusted under 35 U.S.C. 154(b) by 493 days.

(21) Appl. No.: 10/289,725

(22) Filed: Nov. 7, 2002

(65) Prior Publication Data

US 2004/0005540 A1 Jan. 8, 2004

Related U.S. Application Data

(60) Provisional application No. 60/340,017, filed on Nov. 7, 2001, provisional application No. 60/415,037, filed on Oct. 1, 2002.

(51) Int. Cl.
*G01N 33/543* (2006.01)

(52) U.S. Cl. ...................... 436/518; 436/528; 436/529; 436/530; 435/4; 435/5; 435/7.1; 435/7.2

(58) Field of Classification Search ................ 436/518, 436/528, 529, 530; 422/131, 134; 435/4, 435/5, 7.1, 7.2
See application file for complete search history.

(56) References Cited

U.S. PATENT DOCUMENTS

| | | | | |
|---|---|---|---|---|
| 4,459,359 | A * | 7/1984 | Neurath | 435/5 |
| 5,039,611 | A | 8/1991 | Fradet | |
| 5,223,409 | A | 6/1993 | Ladner et al. | |
| 5,403,484 | A | 4/1995 | Ladner et al. | |
| 5,571,698 | A | 11/1996 | Ladner et al. | |
| 5,723,286 | A | 3/1998 | Dower et al. | |
| 5,858,801 | A | 1/1999 | Brizzolara | |
| 5,874,047 | A | 2/1999 | Schoning et al. | |
| 5,922,183 | A | 7/1999 | Rauh | |
| 6,329,501 | B1 | 12/2001 | Smith et al. | |

FOREIGN PATENT DOCUMENTS

DE 197 45 668 A1 4/1998

OTHER PUBLICATIONS

Hengerer (I) et al. (Biosensors & Bioelectronics (1999) vol. 14, p. 139-144).*

(Continued)

*Primary Examiner*—Long V. Le
*Assistant Examiner*—Jacob Cheu
(74) *Attorney, Agent, or Firm*—Alston & Bird LLP

(57) ABSTRACT

Methods and compositions for identifying and characterizing one or more ligands of a peptide are provided. In particular, the invention provides a phage ligand sensor device (PLSD) comprising a sensor coupled to a binding element of interest. Binding elements of interest comprise phage displaying at least one foreign peptide. The PLSD and assays find particular use in identifying and characterizing ligand-peptide interactions.

3 Claims, 10 Drawing Sheets

OTHER PUBLICATIONS

Hengerer (II) et al. (BioTechniques (1999) vol. 26, p. 956-963).*
Iqbal et al. (Biosensor & Bioelectronics 2000, vol. 15, p. 549).*
Pentrenko et al. (Protein Engineering (2000) vol. 13, p. 589).*
Golam, et al., "Dual-mode Acoustic Wave Biosensors Microarrays," *Proceedings of SPIE The International Society of Optical Engineering*, 2003, pp. 129-139, Section 5119.
Nakamura, et al., "Quartz Crystal Microbalance Sensor Targeting Low Molecular Weight Compounds Using Oligopeptide Binder and Peptide-Immobulized Latex Beads," *Analytica Chimica Acts*, 2002, pp. 183-188, vol. 469.
Priohaska, et al., "Affinity Measurements of Antibody Fragments on Phage by Quartz Crystal Microbalance," *Antibody Engineering*, 2001, pp. 397-406.
U.S. Appl. No. 09/438,150, filed Nov. 10, 1999.
U.S. Appl. No. 09/452,968, filed Dec. 2, 1999.
U.S. Appl. No. 09/947,137, filed Sep. 5, 2001.
U.S. Appl. No. 10/068,570, filed Nov. 6, 2002.
Scott, J. and Smith, G., "Searching for Peptide Ligands with an Epitope Library," *Science*, 1990, pp. 386-390, vol. 249.
Smith, G. and Petrenko, V., "Phage Display," *Chemical Reviews*, 1997, pp. 391-410, vol. 97.
Sidhu, "Engineering M13 for Phase Display," *Biomolecular Engineering*, 2001, pp. 57-63, vol. 18.
Soleiman, "Recent Developments in Piezoelectric Immunosensors," *Analyst*, 1994, pp. 2279-2282, vol. 119.
Weiss, G. and Sidhu, S., "Design and Evolution of Artificial M13 Coat Proteins," *J. Mol. Biol*, 2000, pp. 213-219, vol. 300.
Ziegler, C., et al., "Bioelectronic Noses: A Status Report. Part II," *Bisensors & Bioelectronics*. 1998, pp. 539-571, vol. 13.
Barry, M, et al., "Toward Cell-Targeting Gene Therapy Vectors: Selection of Cell-Binding Peptides from Random Peptide-Presenting Phage Libraries," *Nature Medicine*, 1996, pp. 299-305, vol. 2.
Beckett, D., et al., "A Minimal Peptide Substrate in Biotin Holoenzyme Synthetase-Catalyzed Biotinylation," *Prot. Sci.*, 1999, pp. 921-929, vol. 8.
Decker, J., et al., "Characterization of a Human Pancreatic Secretory Trypsin Inhibitor Mutant Binding to *Legionella pneumophila* as Determined by a Quartz Crystal Microbalance," *J. Immunol. Method.*, 2000, pp. 159-1965, vol. 233.
Gau, J., et al., "A MEMS Based Amperometric Detector for *E. coli* Bacteria Using Self-Assembled Monolayers," *Biosensors & Bioelectronics*, 2001, pp. 745-755, vol. 16.
Hengerer, A., et al., "Determination of Phase Antibody Affinities to Antigen by a Microbalance Sensor System," *Biotechniques*, pp. 956-964, vol. 26.
Kishchenko, G., et al., "Structure of a Foreign Peptide Displayed on the Surface of Bacteriophage M13," *J. Mol. Biol.*, 1994, pp. 208-213, vol. 241.
Kouzmitcheva, G., et al., "Identifying Diagnostic Peptides for Lyme Disease through Epitope Discovery," *Clinical & Diagnostic Laborartory Immunology*, 2001, pp. 150-160, vol. 8.
Kramer, R., and Karpen, J., "Spanning Binding Sites on Allosteric Proteins with Polymer-Linked Ligand Dimers," *Nature*, 1998, pp. 710-713, vol. 395.
Kunkel, T., et al., "Rapid and Efficient Site-Specific Mutagensis without Phenotypic Selection," *Meth. Enzymol.*, 1987, pp. 367-382, vol. 154.
Luppa, P., et al., "Immunosensors—Principles and Applications to Clinical Chemistry," *Clinica Chimica Acta*, 2001, pp. 1-26, vol. 314.
Pasqualini, R. and Ruoslahti, E., "Organ Targeting in vivo Using Phage Display Peptide Libraries," *Nature*, 1996, pp. 364-366, vol. 380.
Pathirana, S., et al., "Rapid and Sensitive Biosensor for *Salmonella," Biosensors & Bioelectronics*, 2000, pp. 135-141, vol. 15.
Petrenko, V., et al., "A Library of Organic Landscapes on Filamentous Phage," *Protein Engineering*, 1996, pp. 797-801, vol. 9(9).
Petrenko, V. and Smith, G., "Phages from Landscape Libraries as Substitute Antibodies," *Protein Engineering*, 2000, pp. 589-592. vol. 13(8).
Romanov, V., et al., "Phage Display Selection of Peptides that Affect Prostate Carcinoma Cells Attachment and Invasion," *Prostate*, 2001, pp. 239-251, vol. 47.
Schumacher, T., et al., "Identification of D-Peptide Ligands Through Mirror-Image Phage Display," *Science*, 1996, pp. 1854-1857, vol. 271.

* cited by examiner

PHAGE LIGAND SENSOR DEVICES AND USES THEREOF

CROSS-REFERENCE TO RELATED APPLICATIONS

This Application claims the benefit of U.S. Provisional Application No. 60/340,017, filed Nov. 7, 2001, and U.S. Provisional Application No. 60/415,037, filed Oct. 1, 2002, which disclosures are herein incorporated.

FEDERALLY SPONSORED RESEARCH OR DEVELOPMENT

The research underlying this invention was supposed in part with funds from the National Institutes of Health, Grant No. NIH-1-R21-A105564501, and the Department of Army, Grant No. DAAD 19-01-1-0454. The United States Government may have an interest in the subject matter or this invention.

FIELD OF THE INVENTION

The invention relates to sensors for the detection of ligands of interest and uses thereof.

BACKGROUND OF THE INVENTION

Many applications require detection and identification of ligands, or molecules having particular binding properties. The binding properties of a particular ligand may be detected and characterized by the use of appropriate sensors. "Biosensors" have been reported in the literature and provide an alternative model for molecular screening. Biosensors are made up of an analytical platform and a binding entity to which the ligand may bind. The detection of a ligand by a biosensor requires a ligand which binds the binding entity and an analytical platform or sensor which generates a detectable signal that can be measured. The analytical platforms measure changes in mass, capacitance, resistance, surface plasma resonance, reflectometric interference, etc. resulting from the interaction of the ligand with the binding entity.

The current state of the art in biosensor technology includes a number of biosensor designs. For example, U.S. Pat. No. 6,241,863 (with inventor Monbouquette) describes the development of amperometric biosensors based on redox enzymes. U.S. Pat. No. 6,239,255 describes surface plasmon resonance biosensors. Still other biosensors have been described, including biosensors which utilize functionalized microspheres for optical diffraction (U.S. Pat. No. 6,221,579), mass-sensitive biosensors (U.S. Pat. No. 6,087,187), hybrid biosensors (U.S. Pat. No. 6,051,422), metal oxide matrix biosensors (U.S. Pat. No. 5,922,183), silicon-based biosensors (U.S. Pat. No. 5,874,047), solid-supported membrane biosensors (U.S. Pat. No. 5,846,814), fiber-optic chemiluminescent biosensors (U.S. Pat. No. 5,792,621) and others.

Biosensors previously reported in the literature are somewhat limited because the reported devices have low sensitivity, limited longevity, and/or long response times. Decker et al. ((2000) *J. Immunol. Methods* 233:159-165) reported that more than 90 minutes were needed to measure phage binding by peptide fragments immobilized by biotin/streptavidin coupling. Hengerer et al. ((1999) *Biotechniques* 26: 956-60, 962, 964) reported binding of phage antibodies to antigen immobilized on a quartz crystal microbalance with a time constant of about 100 min. These long response times are not compatible with rapid screening and make large-scale screening unwieldy. Therefore, there remains a need for a biosensor which can rapidly detect specific proteins.

In addition, reported biosensors generally suffer from disadvantages such as low specificity and low affinity. Some biosensor platforms utilize antibodies as the binding element. For example, U.S. Pat. No. 5,922,183 teaches the use of thin film composites of metal oxides and antibodies for amperometric and potentiometric sensing. Porous silicon biosensors are described for use with antibodies in U.S. Pat. No. 5,874,047. A patterned multiple antibody substrate for use in biosensors or immunosensors was prepared by adsorbing specific antibodies at the sites in U.S. Pat. No. 5,858,801. U.S. Pat. No. 5,039,611 teaches the use of monoclonal antibodies to superficial papillary bladder tumor cells in an ELISA-type format. See also, copending U.S. application Ser. No. 09/452,968, filed Dec. 2, 1999.

Antibody-based sensors represent an improvement over previously-used sensors in several ways, and can exhibit improved specificity and affinity (see, e.g., Ziegler et al. (1998) *Biosensors & Bioelectronics* 13: 539-571. However, antibody-based sensors have several disadvantages which restrict their usefulness, including high cost and short longevity or inability to perform in various environmental or field test conditions. Moreover, the quality of antibodies can vary with different production variables, such as the animal used to produce the antibodies. Another disadvantage of antibodies is that it may take months to generate the desired antibodies for use in an antibody-based sensor.

The threat of bioterrorism highlights the need for specific, accurate sensors that are rapidly prepared. At present, the earliest recognition of and response to a bioterrorist attack with *Bacillus anthracis* (anthrax) spores may be based on clinical manifestations of anthrax and laboratory culture tests, which require days to complete (Inglesby et al. (1999) *JAMA* 281: 1735-45). Thus, a need exists for specific, accurate biosensors that are rapidly prepared.

SUMMARY OF THE INVENTION

The invention provides phage ligand sensor devices ("PLSDs") that comprise a piezoelectric sensor coupled to a binding element. The binding element is landscape phage displaying at least one foreign peptide. The invention allows detection and characterization of ligands which bind to the binding element. In this manner, the invention provides an in vitro assay to detect and examine interactions between ligands and binding elements. Thus, the invention provides an assay for the rapid discovery of ligands specific to various peptides and finds use in the detection of a wide range of biological, organic, and other materials.

BRIEF DESCRIPTION OF THE DRAWINGS

In FIG. 9A, relative ELISA signal is shown as a function of b-galactosidase concentration (nanomolar). Results demonstrated that the affinity of the phage-ligand complex depended on the mode of phage immobilization and type of analytical platform: 30 nM for ELISA (circles) and 0.6 nM for the PLSD (squares).

FIG. 9B shows a Hill presentation of binding curves (Y/1-Y is shown as a function of b-galactosidase concentration (nanomolar). The observed binding valence of the ligand to the phage biosensor (squares) was 2.14, while for the ELISA format (circles) the observed binding valence was 1.02. The difference in affinities (FIG. 9A) can be attributed to the monovalent (ELISA) versus divalent (PLSD) interaction of the phage with the b-galactosidase ligand.

DETAILED DESCRIPTION OF THE INVENTION

Methods and compositions for identifying and/or evaluating one or more ligands are provided. In particular, phage ligand sensor devices (PLSDs) are provided, as well as assays using phage ligand sensor devices. The PLSD comprises a sensor device coupled to a binding element. The PLSD allows detection and characterization interactions between the binding element and one or more ligands. In this manner, the PLSD provides an in vitro assay that can be used to isolate and examine ligands that bind to particular peptides and thus provides an assay for the rapid discovery of small molecule ligands specific to peptides of interest. Thus, PLSDs find use in many applications. For example, the PLSDs and assays of the invention are useful in the isolation and identification of peptide-specific molecules that can be used to target various compounds or molecules in gene and/or drug therapy protocols.

The binding element component of PLSDs comprises engineered bacteriophage, also referred to herein as “phage” or “landscape phage.” Phage are well-suited to the requirements of PLSDs due to their life cycle and physical structure. Filamentous phage such as M13, fl and fd are thread-shaped bacterial viruses. The outer coat of these phage is composed of thousands of 50-residue α-helical subunits of the major coat protein pVIII which overlap one another to form a tube encasing the viral DNA. Several copies of each of four minor coat proteins, including pIII and pVI, form the tips of this tubular sheath.

Figure 1:
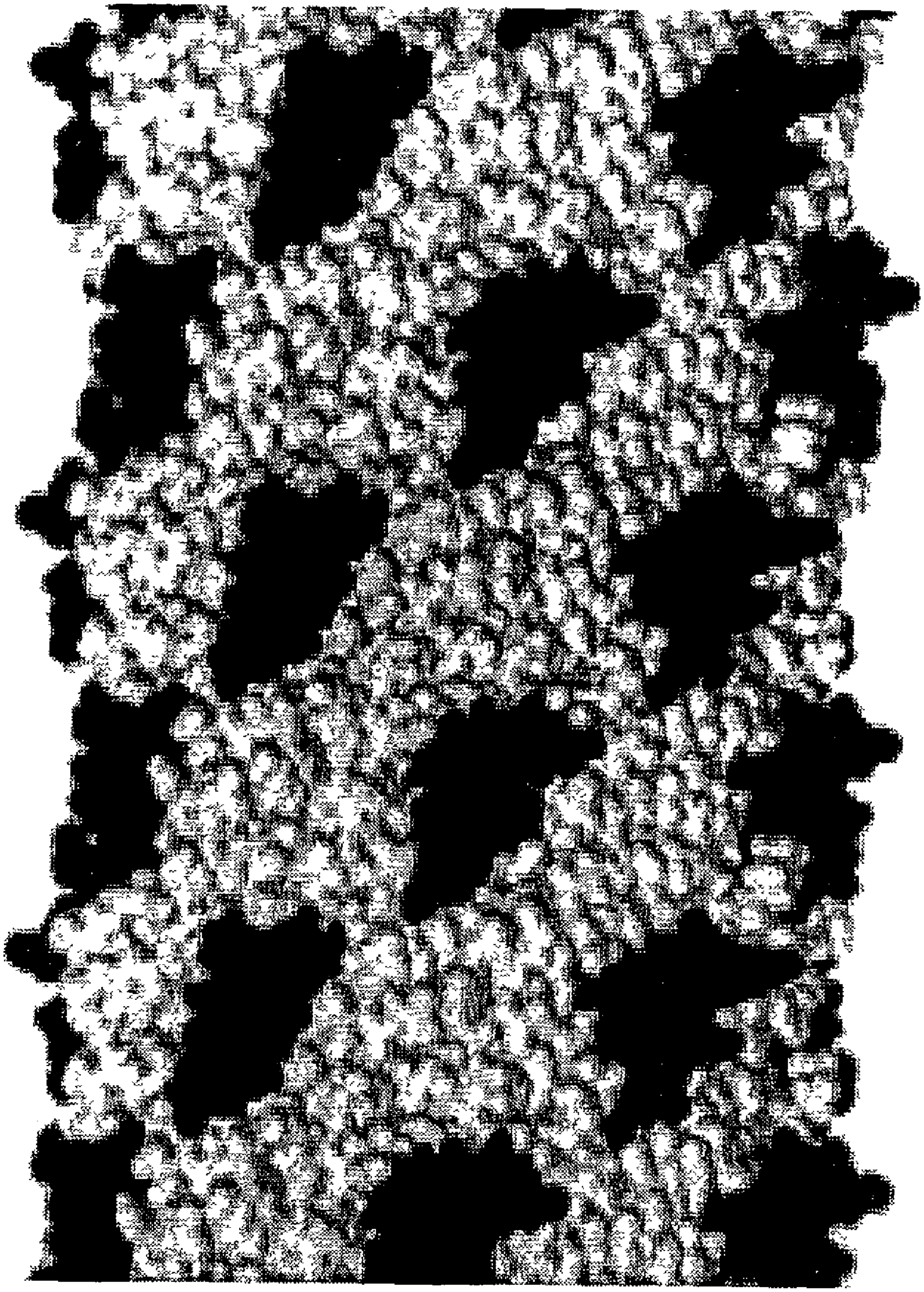
FIG. 1 shows a molecular model of a landscape phage in which altered amino acids (black) are displayed against a background of wild-type phage amino acids (gray).

For use as the binding element of PLSDs, phage are engineered to produce foreign peptides rather than the wildtype or native phage coat protein pVIII. To create engineered phage, at least one short foreign coding sequence is spliced or substituted into the pVIII gene so that an altered or foreign amino acid sequence is displayed on every pVIII subunit (see FIG. 1, showing about a one percent section of a viral sheath from an engineered phage). The amount of alteration which can be made to the pVIII gene is limited only by the physical limitations of the phage and the requirements of the PLSD; any alteration may be made so long as the resulting phage can be used to assemble a functional PLSD. Thus, the term “foreign peptide” encompasses pVIII proteins in which as few as one amino acid residue is altered. Thus, a foreign peptide may have the native sequence of a pVIII protein except for 1, 2, 3, 4, 5, 6, 7, 8, 9, 10, 11, or 12 or more amino acid alterations. The term “foreign peptide” encompasses embodiments in which the altered pVIII gene comprises multiple altered amino acid residues interspersed with unaltered, or wildtype, pVIII amino acid residues (see Example 2). Where the altered amino acid sequence is derived from a native protein, the altered sequence may represent only a small portion, or fragment, of the native amino acid sequence from which it is derived. In this manner, a foreign peptide that comprises a portion or fragment of a native protein may be said to be derived from that native protein.

Methods and compositions for creating engineered phage are known in the art (see Petrenko et al. (1996) *Protein Engineering* 19(9): 797-801). In such an engineered phage, the foreign peptide is identical in all the coat proteins or subunits of a single virion. Thus, in some embodiments, the assembled phage viral sheath will have a structure essentially as depicted in FIG. 1, where altered amino acids are interspersed with the wild-type amino acids in a "landscape" to which ligands may bind. The foreign peptide can adapt various conformations depending on composition and sequence of amino acids that form the peptide, so in some embodiments the foreign peptide will protrude from the surface of the viral sheath.

The structure of engineered phage expressing foreign peptides in this manner can be likened to the complementarity determining regions (CDRs) of antibodies. Like CDRs, the foreign peptides are highly variable, and because they are generally forced to lie up against the virus body, they are in many instances constrained by interactions with neighboring wild-type residues to form a defined organic "landscape" (see FIG. 1), which led to the term "landscape phage" to describe these engineered phage. In addition, phage may be affinity-selected to bind to one of many different ligands. See Petrenko and Smith (2000) *Protein Engineering* 13(8): 589-592; Romanov et al. (2001) *Prostate* 47: 239-251. Phage have many properties which make them superior binding elements for biological sensor devices and particular applications of such devices. For example, affinity selection and propagation of phage which bind to a particular peptide takes as little as several weeks to complete, in contrast to the selection of antibodies, which typically takes several months.

Phage can also be engineered to create phage-display libraries, as is well-known in the art. A phage-display library is a collection of engineered phage, each of which contain a short foreign coding sequence spliced into the major coat protein gene so that the altered amino acids are displayed on every coat protein subunit. A phage-display library as a whole can represent billions of different peptides altogether. The peptide specified by the foreign coding sequence is displayed on the surface of the phage or virion (as diagrammed in FIG. 1). Each phage clone displays many copies of a single foreign peptide, but a library as a whole may represent billions of peptides altogether. Because the viral carrier is infective, phage can be cloned individually, and either whole libraries or individual clones can be propagated indefinitely. Phage-display technology is well-known in the art. See, for example, Scott & Smith (1990) *Science* 249: 386-390; Sidhu (2001) *Biomol. Eng.* 18(2): 57-63; Kischenko et al. (1994) J. Mol. Biol. 241: 208-213. Random peptide libraries are also known in the art (see, for example, Barbas 3d (1993) *Curr. Opin. Biotechnol.* 4(5): 526-530), and a billion-clone library of filamentous phage with different surface structures was demonstrated by Petrenko et al. (1996) *Protein Engineering* 19(9): 797-801. Several U.S. patents describe random peptide libraries, including: U.S. Pat. No. 5,723,286 (with inventor Dower); U.S. Pat. No. 5,223,409 (with inventor Ladner); U.S. Pat. No. 5,403,484 (with inventor Ladner); and U.S. Pat. No. 5,571,698 (with inventor Ladner).

The surface density of a phage particle is 300-400 $m^2/g$, a density which exceeds probably the best-known catalysts and competes well with good adsorbents such as activated charcoal (see information available at the URL www_.ilpi.com/msds/ref/activatedcharcoal.html) and mesoporous zirconia particles (NexTech Materials; see information available at the URL www.fuelcellmaterials.com/mesoporous_zirconia_catalyst.htm). Phage expressing foreign peptides provide an extremely high multivalency of thousands of binding sites per phage particle. In this manner, the PLSDs of the invention provide superior binding properties. In addition, phage structure is extraordinarily robust, being resistant to heat (up to 70° C.), many organic solvents (e.g., acetonitrile), urea (up to 6 M), acid, alkali and other stresses. Purified phage can be stored indefinitely at moderate temperatures without losing infectivity.

Figure 9:
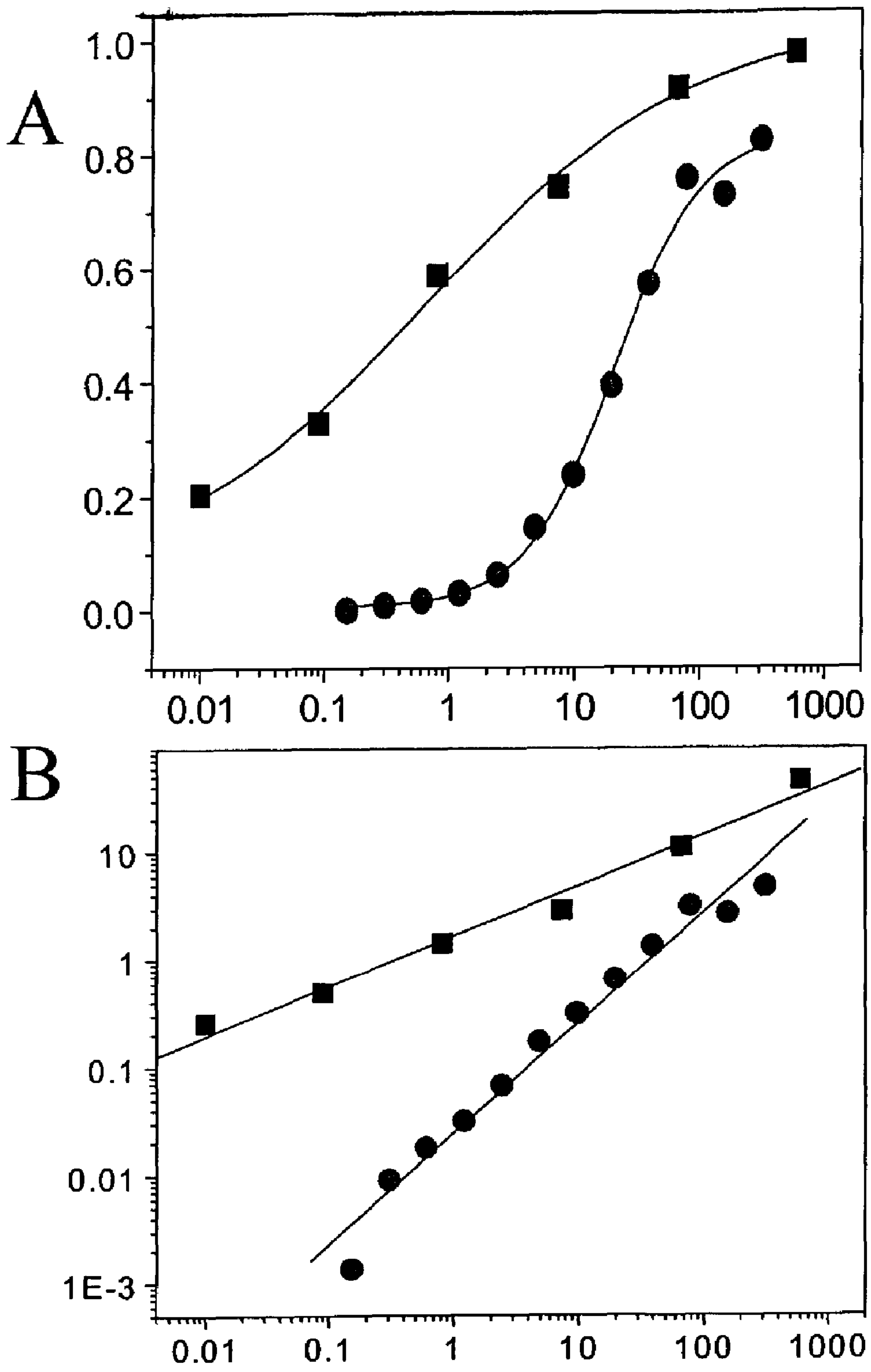
FIG. 9 shows results of experiments comparing the dose-dependent binding of b-galactosidase to phage immobilized to an ELISA plate and as the binding element of a PLSD with a TSM quartz sensor.
Figure 10:
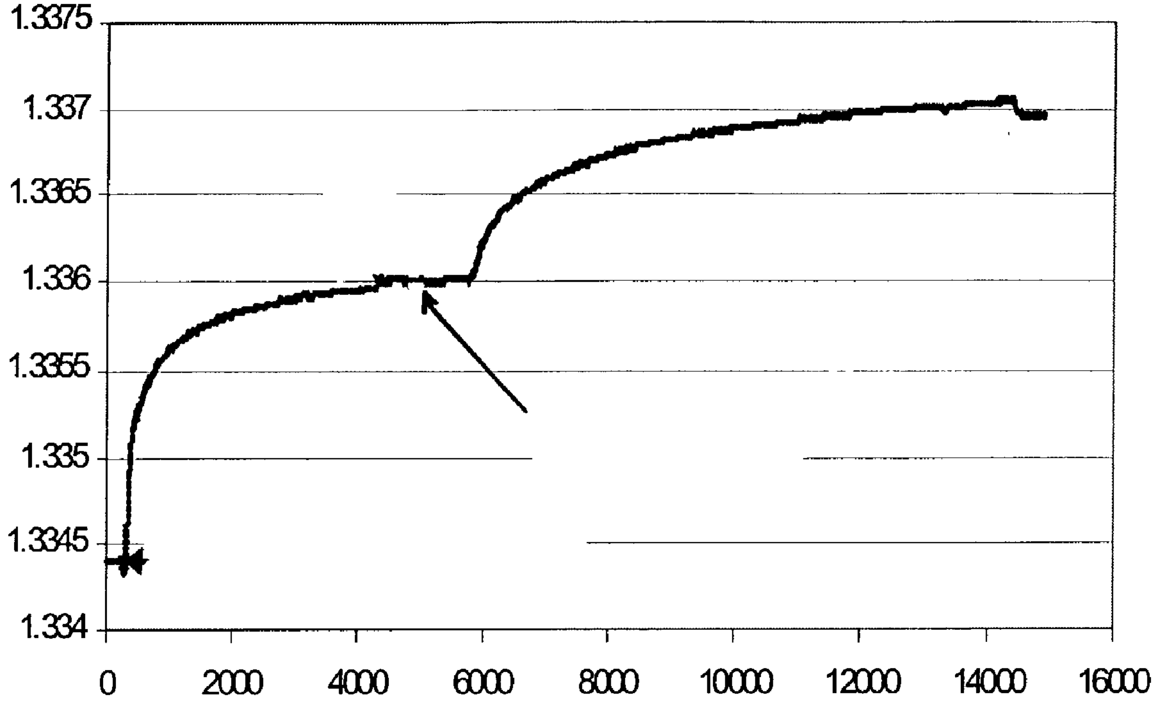
FIG. 10 shows output from a PLSD assembled using phage selected against β-galactosidase as the binding element and an SPR sensor (see Example 1). This PLSD demonstrated strong binding to β-galactosidase. Refractive Index is graphed as a function of time (seconds). The arrow indicates exposure of the sensor to β-galactosidase.

By selecting a particular method of biotinylation (further discussed herein below) and controlling the density of phage on the sensor as well as other properties of the phage, coupling composition or method, and sensor, phage arrays may be assembled that have optimal properties for the assay of interest. Binding elements comprising very dense, linear phage arrays ("velvet-type" arrays) tend to exhibit monovalent binding behavior, while less-dense, largely non-linear phage arrays ("felt-type" array) tend to exhibit multivalent binding behavior. The multivalent interaction, widely used in biological and chemical systems for increasing affinity of binding due to avidity, has been effectively used in other contexts to enhance affinity. Affinity has been shown to increase as much as a thousand fold where the binding valence increased from monovalent to divalent binding (see Kramer and Karpen (1998) *Nature* 395:710-713). With one embodiment of a PLSD of the invention, it was observed that the valence of ligand binding in an ELISA format was 1, while the valence of ligand binding to a PLSD was 2 (Example 4). Surprisingly, this increase in binding valence by a factor of two resulted in a 50-fold increase in affinity as the value of the binding constant increased from 30 nM for the ELISA format to 0.5 nM for the PLSD (Example 4; FIGS. 9A and 9B). Thus, PLSDs of the invention provide very high binding affinities. Furthermore, the immobilized phage of the binding element can create an extremely high concentration of binding sites, even reaching 0.1 M in a velvet-type layer, so that a binding element comprising a velvet-type phage array is capable of increasing the concentration of ligand (on the PLSD surface) by a factor of up to a billion.

As binding elements of a biosensor device, phages with high avidity can provide practically irreversible binding of polyvalent antigens such as bacteria and viruses. This property of a PLSD may be useful in detection of very low concentrations of microorganisms in a large liquid sample, or a flow of liquid sample over the biosensor. This property may also be useful in detecting ligands which are present in a gas, such as for example ambient air, and in this manner the PLSDs of the invention can provide detection of airborne contaminants such as, for example, toxic gases or bacterial spores.

Another advantage of the present invention is the ease with which phage can be produced for use in a PLSD device. Filamentous phage are efficiently and conveniently produced using bacterial cell cultures. The yield of wild-type phage particles from bacterial cultures regularly reaches 300 mg/liter, although engineered phage particles tend to have lower yields, e.g., 20 mg/liter for engineered or landscape phage. The phage particles are secreted from the cell nearly free of intracellular components, and further purification is easily accomplished by simple, routine steps that are applicable to any phage.

Thus, the invention provides compositions and assays for the rapid discovery of ligands specific to various peptides and finds use in the detection of a wide range of biological, organic, and other materials. A ligand is any compound, particle, or organism that binds at some measurable level to at least one foreign peptide displayed on landscape phage of the PLSD, thereby producing a detectable signal by a PLSD of the invention. Thus, ligand binding is detected and can be quantitated using a PLSD of the invention. Ligands as well as peptides of interest may be isolated or derived from any organism or species, including but not limited to mammals, reptiles, amphibians, plants, bacteria, viruses, amoeba, rickettsia, etc.

The PLSDs of the invention find use in detecting ligands such as, for example, enzymes, bacteria, viruses and other biological or organic agents and/or compounds as well as synthetic or artificial agents and/or compounds. Any ligand that is capable of binding to a foreign peptide displayed on a landscape phage may be detected and evaluated using the compositions and methods of the invention. More than one ligand may bind to a particular foreign peptide.

Thus, a ligand that binds to a particular foreign peptide may be but is not limited to microorganisms, including bacteria, viruses, fungi, and protozoa as well as organic and inorganic chemical compounds. Thus, ligands may include pathogens or harmful agents which are viruses, bacteria, fungus, prions, rickettsia, amoeba, and natural and synthetic toxins. Ligands may also include biochemical compounds, such as, for example, proteins, peptides, and nucleic acids. The term "virus" as used herein encompasses any virus, for example, smallpox virus, yellow fever virus, cholera virus, and hemorrhagic fever viruses such as Ebola virus, Marburg virus, and Lassa fever virus. The term "bacteria" as used herein encompasses bacterial spores and includes any species of bacteria, such as, for example, those bacteria known to cause bubonic plague (e.g., *Yersinia pestis*), pneumonic plague, and anthrax (e.g., *Bacillus anthracis*). Harmful agents and toxins include but are not limited to organic toxins such as ricin, botulism toxin (e.g., *Clostridium botulinum* toxin), aflatoxin, *Clostridium perfringens* toxin, and Staphylococcal enterotoxin B.

Phages that are useful in the compositions and methods of the invention display a foreign peptide of interest and are thus engineered phages. Engineered phages can be generated, identified, and isolated as expressing any foreign peptide, which may comprise a particular amino acid sequence referred to as a "peptide of interest." Where the peptide of interest is specific to a particular cell type or tissue, or to a tissue affected by a particular disease or disorder, phage expressing that peptide of interest may be used to identify and isolate compounds which bind the particular peptide of interest. Such compounds may be useful for delivery of compounds to the particular cell type or tissue, or they may themselves be useful in treating the particular cell type or tissue from which the peptide of interest was isolated. In this manner, peptides of interest may be associated primarily with a disease or disorder, such as a tumor or particular type of tumor. Based on the selective binding protocols, compounds which are tissue-type specific or alternatively which are capable of binding to different cells can be determined. In the same manner, peptides of interest may be species independent, that is, the peptides are associated with the same tissue type or cell type from any species. Alternatively, the peptides may be species-specific. By species-specific is intended that the peptides are specific to particular tissue cells (e.g., liver) from a particular species and will not bind to the same tissue cells from another species. Peptides of interest may be isolated from any species. Mammalian species of interest include, but are not limited to human, rat, dog, chimpanzee, etc.

Peptides of interest may be specific to a particular cell culture, cell type, tissue, stage of development, or disease or disorder or they may be preferentially associated with a particular cell type, stage of development, or disease or disorder. Peptides of interest may also be generally expressed by more than one tissue, or by many tissues, or may be associated with many tissue states. Once a peptide of interest is identified, a coding sequence corresponding to the peptide may be determined and a synthetic nucleotide sequence created to replace the phage major coat protein pVIII with the foreign peptide. This nucleotide sequence is then used with standard techniques to generate landscape or engineered phages comprising the fusion protein, and these phages are used to create a PLSD of the invention. See, e.g., Ivanenkov et al. (1999) *Biochim. Biophys. Acta* 1448: 450-62, entitled "Uptake and intracellular fate of phage display vectors in mammalian cells," as corrected in Ivanenkov et al. (1999) *Biochim. Biophys. Acta* 1451: 364.

Methods are available in the art for the identification and isolation of peptides of interest. Such methods can include selection from a bacteriophage (phage) library which expresses random peptides, mirror image phage display to isolate naturally-occurring L-enantiomers in a peptide library, and the like. See, for example, Barry et al. (1996) *Nature Medicine* 2:299-305; Schumacher et al. (1996) *Science* 271:1854-1857; Pasqualini et al. (1996) *Nature* 380: 364-366; U.S. Pat. No. 6,329,501, issued Dec. 11, 2001, and the references cited therein, herein incorporated by reference. Peptides of interest can also be selected based on, for example, the sequence of cell surface proteins or by in vivo phage display screening as discussed in copending applications application Ser. No. 09/947,137, filed Sep. 5, 2001, and application Ser. No. 09/438,150, filed Nov. 10, 1999, herein incorporated by reference. See also co-pending U.S. application Ser. No. 10/068,570, filed Feb. 6, 2002, hereby incorporated by reference. Thus, peptides of interest need not be identified by the in vivo phage display screening method, but may be known in the art or identified or produced using other techniques or expertise. Peptides of interest may also be random peptides, i.e., peptides with random amino acid sequences, or the amino acid sequence may be designed.

Once peptides of interest or foreign peptides have been selected, they may be modified by any suitable method. Such methods include random mutagenesis, as well as synthesis of the compounds for selected amino acid substitutions. Peptides of various length can be constructed and tested for the effect on binding affinity and specificity of a test ligand. The compositions and assays of the invention may also be used to evaluate variants of the peptide sequence(s) for enhanced affinity to a particular ligand, such as, for example, a phage that binds strongly to the original peptide or a similar peptide.

A nucleotide sequence encoding the peptide of interest is used in the construction of foreign proteins, coding regions, or vectors for use in the invention. Such methods are known in the art (see, e.g., Smith and Petrenko (1997) *Chemical Reviews* 97: 391-410, and references cited therein). Additionally the construction of expression cassettes are known as well as promoters, terminators, enhancers, etc., necessary for expression. By nucleotide is intended gene sequences, DNA, RNA, as well as antisense nucleic acids. Standard techniques for the construction of the nucleotides of the present invention are well-known to those of ordinary skill in the art and can be found in such references as Sambrook et al (2001) *Molecular Cloning: A Laboratory Manual* (3d ed., Cold Spring Harbor Laboratory). A variety of strategies are available for ligating fragments of DNA, the choice of which depends on the nature of the termini of the DNA fragments and which can be readily determined and accomplished by those of skill in the art.

A bacteriophage or "phage" which is a binding element of the invention can be created using prior knowledge about a foreign peptide, as discussed above, and can also be identified and isolated from phage libraries as having particular binding properties. Such binding properties can include, for example, the ability to bind to a particular ligand as well as the ability to bind receptors or antibodies. See, for example, Barry et al. (1996) *Nature Medicine* 2:299-305; Devlin et al. (1990) 249:404-406; Cwirla et al. (1990) *Proc. Natl. Acad. Sci. USA* 87:6378-6382; and the references cited therein. Thus, a bacteriophage which is a binding element of the invention may be selected from a phage display library that was constructed utilizing a number of peptides having random or partially random amino acid sequences. Phage may also be created and selected after multiple rounds of sequence mutagenesis and affinity selection. See, for example, Tuckey and Noren (2002) *J. Immunol. Methods* 270: 247; Chu et al. (2002) *J. Mol. Biol.* 323: 253.

Any phage may be used as a binding element of the invention so long as it may be used to create a PLSD of the invention and is capable of binding to a ligand. Methods for preparing libraries containing diverse populations are also disclosed in Gordon et al. (1994) *J. Med. Chem.* 37:1385-1401; Ecker and Crooke (1995) *BioTechnology* 13:351-360; Goodman and Ro, "Peptidomimetics For Drug Design," in *Burger's Medicinal Chemistry and Drug Discovery*, Vol. 1, M. E. Wolff (ed.) John Wiley & Sons 1995, pages 803-861; Blondelle et al. (1995) *Trends Anal. Chem.* 14:83-92; Sambrook et al. (2001) *Molecular Cloning: A Laboratory Manual* (3d ed., Cold Spring Harbor Laboratory); and Ausubel et al. (eds). (1998) *Current Protocols in Molecular Biology* (John Wiley & Sons). Each of these references is herein incorporated by reference. The foreign peptide and/or landscape phage may optionally be further engineered or adapted to enhance the performance of the PLSD. Methods for engineering nucleotides, peptides, and phage are known in the art. See, e.g., methods reviewed in Smith and Petrenko (1997) *Chemical Reviews* 97: 391-410.

Engineered phage are coupled to a sensor to create the PLSD of the invention. When coupled to the sensor, phage are capable of interacting with ligands and this interaction is detected by the sensor. In some embodiments, attachment of phage to the sensor is accomplished using the N-terminal amino-groups or amino-butyl groups of the $Lys_{10}$ residue of the major coat protein. Cross-linkers for this purpose are commercially available, and one of skill in the art can readily select an appropriate cross-linker or combination of coupling compositions to produce the PLSDs of the invention. In some embodiments, the sensor is prepared by the addition of one or more layers to which the phage will bind, and the preparation of the phage to be coupled to the sensor simply comprises ensuring that the phage are at a proper concentration for addition to the prepared sensor. In other embodiments, the sensor is prepared by thorough cleaning and the phage are directly bound to the gold sensor surface by interaction with the phage tip (i.e., the pIII protein). For a "brush-type" conjugation of the phages to the sensor device, a tag peptide such as streptavidin-binding peptide HPQ or a biotinylation site can be engineered into the minor coat protein pIII located on the tip of the phage. The phage can then be conjugated non-covalently to a streptavidin-coated sensor device. In other embodiments, where a streptavidin-binding "tag" peptide is engineered into the phage, the sensor can be prepared with a Langmuir-Blodgett film of biotinylated phospholipid. In such embodiments, the assembly of the PLSD may be accomplished by the addition of streptavidin to couple the landscape phage to the sensor. Any coupling method or composition may be used so long as the landscape phage is attached to the sensor so as to permit detection of ligand binding. Thus, in some embodiments, a sensor is coated with gold or a gold-coated sensor is obtained; the sensor is then coated with streptavidin and coupled via biotin to the landscape phage. Alternatively, the coupling composition layer may comprise a biotinylated thiol or disulfide layer which is linked directly to a layer of gold; the biotinylated layer is then linked to streptavidin and coupled via biotin to the landscape phage. See, for example, Luppa et al. (2001) *Clinica Chimica Acta* 314: 1-26; Gau et al. (2001) *Biosensors & Bioelectronics* 16: 745-755.

In some embodiments, the binding element of PLSDs of the invention comprises a single strain of phage so that each phage on the PLSD is genetically identical (excepting rare mutations that may occur during phage replication and are not expected to affect the performance of the binding element). In other embodiments, the binding element comprises multiple strains of phage, so that each strain of phage displays a different foreign peptide. Thus, binding elements that comprise multiple strains of phage are designed to bind to more than one ligand. The strains of phage to be used in such embodiments are selected based on desired properties of the sensor, which will vary with the particular application for which the PLSD is to be used. Thus, for example, a binding element of a PLSD could comprise foreign peptides known to bind to *Bacillus anthracis* and *Yersinia pestis*. In this manner, a PLSD of the invention may be created with more than one variety of landscape phage; i.e., the PLSD may be created using a mixture of landscape phage expressing different foreign peptides, or even a phage library.

The PLSD comprises a piezoelectric sensor. In some embodiments, an acoustic wave sensor is used which comprises an AT-cut planar quartz crystal with a 5 MHz nominal oscillating frequency. Such crystals, suitable for acoustic wave devices (AWD), are commercially available (e.g., Maxtek, Inc). The crystals or sensors may be supplied with electrodes, for example, crystals may be supplied with circular gold electrodes deposited on both sides of the crystal for the electrical connection to the oscillatory circuit. In some embodiments, a mass-sensitive sensor is used; alternatively, other sensors may be used so long as they are capable of detecting ligand binding and providing signal output that changes in response to that binding. A direct correlation of binding and signal output is not required so long as the desired result is obtained. Thus, when binding occurs, different physical and electrochemical properties of the sensor may be changed: mass; free energy; electrical properties such as charge and conductance; optical properties such as fluorescence, luminescence, adsorption, scatter, and refraction. Accordingly, suitable sensors include electrochemical, calorimetric, and optical sensors. See, for example, Luppa et al. (2001) *Clinica Chimica Acta* 314: 1-26. One of skill in the art will appreciate that for different applications of the assays of the invention, sensors with different sensitivities and outputs may be used. Thus, for example, in some applications a preferred PLSD will be capable of high-resolution quantitation of changes in binding, while for other applications a PLSD need only detect the presence or absence of high-affinity binding.

In some embodiments, a Maxtek 740 sensor is used which has a working frequency of 5 MHz. One of skill recognizes that the working frequency corresponding to the highest sensitivity of the PLSD system can be identified to optimize the changes in the resonance frequency of the sensor when ligand is bound. Any suitable device may be used to monitor the signal output from the sensor, for example, an HP4195A Network/Spectrum Analyzer (Hewlett-Packard) can be used. The analyzer device scans a set range of frequencies and measures the signal properties at each frequency. After the optimal frequency is found for a particular phage/ligand combination, this frequency can be used as a working frequency for sensitive measurements of binding; useful frequencies are generally between 2 MHz and 150 MHz.

The sensor may be coupled or linked to the phage by any suitable composition and method so long as the resulting PLSD is capable of detecting ligand binding. In some embodiments, the step of preparing the sensor may simply comprise ensuring that the sensor is clean and ready to be coupled to the phage (see generally, Cunningham (1998) *Introduction to Bioanalytical Sensors* (Wiley-Interscience)). Where at least one composition is added to the sensor surface, the sensor is then said to comprise a coupling composition layer. For example, a Langmuir-Blodgett film of biotinylated lipid can be added to the sensor. Langmuir-Blodgett films are formed from at least one monolayer. A monolayer is a one-molecule-thick film of at least one amphiphilic compound or composition that forms at the air/water interface of an aqueous solution. Each molecule in the monolayer is aligned in the same orientation, with the hydrophobic domain facing the air and the hydrophilic domain facing the aqueous solution. Compression of the monolayer results in the formation of an ordered two dimensional solid that may be transferred to a substrate by passing the substrate through the monolayer at the air/liquid interface. A monolayer that has been transferred to a substrate is termed a Langmuir-Blodgett film, or LB film. For reviews of Langmuir-Blodgett technology, see Gaines, G. L. Jr. (1966) *Insoluble Monolayers at Liquid-Gas Interfaces*, Interscience, New York; Zasadzinski et al. (1994) *Science* 263: 1726-1733; Ullman (1991) *An Introduction to Ultrathin Organic Films*, Academic Press, Boston, Mass.; and Roberts (1990) *Langmuir-Blodgett Films*, Plenum, N.Y.; the contents of which are incorporated herein by reference.

Monolayers are typically composed of organic molecules such as lipids, fatty acids and fatty acid derivatives, fat soluble vitamins, cholesterol, chlorophyll, valinomycin and synthetic polymers such as polyvinyl acetate and polymethyl methacrylate. Monolayers may also be formed by many other amphiphilic compounds; thus, many amphiphilic compounds may be used to form the monolayers of the invention. Such compounds include lipids having at least 14 carbon atoms. Examples include stearic acid and hexadecanoic acid. Other compounds that will form monolayers include, but are not limited to those described in Gaines, G. L. Jr. (1966) *Insoluble Monolayers Liquid-Gas Interface*, Interscience, New York, the contents of which are incorporated by reference.

Lipid monolayer depositions may be carried out by methods known in the art and as described in copending application Ser. No. 09/452,968, filed Dec. 2, 1999, herein incorporated by reference in its entirety. Langmuir-Blodgett (LB) film balances are commercially available, for example from KSV-Chemicals, Finland, and are operated in accordance with the supplier's instructions.

The Langmuir-Blodgett film is formed by the successive transfer of monolayers onto the surface of the sensor using the Langmuir-Blodgett technique. In some embodiments, biotinylated lipid solutions are spread on the aqueous subphase as hexane solutions. The monolayer is then compressed and a vertical film deposition is performed. In LB film deposition, multiple monolayers may be added to the sensor by successive dipping of the sensors through the monomolecular film deposited at the air/liquid interface. LB films may be formed by the addition of one, two three, four, five, six, seven, eight, nine, ten, eleven, twelve, thirteen, fourteen, fifteen or more monolayers in this manner to create the final Langmuir-Blodgett film.

The monolayers used to create the Langmuir-Blodgett film may be formed without the aid of a volatile organic solvent. See, for example, copending application Ser. No. 09/452,968, filed Dec. 2, 1999. Many methods for forming LB films require dissolution of the compounds to be formed into a monolayer in a volatile organic solvent such as hexane. The organic solvent forms a separate phase from the aqueous solution and functions to prevent dissolution of the monolayer components in the aqueous phase. After spreading the mixture at the air/liquid interface of the aqueous solution, the solvent is allowed to evaporate, leaving a monolayer at the interface. However, in such embodiments, the organic solvent may damage the monolayer components and leave an undesirable residue which contributes to background levels of nonspecific binding. Thus, in some embodiments, monolayers formed without the aid of an organic solvent as set forth in copending application Ser. No. 09/452,968, filed Dec. 2, 1999, provide improved properties to the PLSDs of the present invention. In some embodiments, a landscape phage is covalently bound or linked to phospholipids; vesicles comprising these phospholipids are then used to create monolayers and LB films to make a PLSD of the invention. In such embodiments, the coupling of the phage to the sensor may be accomplished by the formation of such an LB film on the sensors and does not necessarily require a coupling via streptavidin and biotin interactions. Such sensors may be gold-plated or coated with other material to facilitate the adherence of the LB film to the sensor.

"Monolayer" as used herein, refers to a one molecule thick film of at least one amphiphilic compound or composition. "Piezoelectric" as used herein, refers to the ability to generate a voltage when mechanical force is applied, or to generate a mechanical force when voltage is supplied. This reciprocal relationship is referred to as the piezoelectric effect. The absence of a center of symmetry in the piezoelectric crystal is necessary for the piezoelectric effect. Of the 21 classes of crystals that lack a center of symmetry, all but one class are piezoelectric. For example, a quartz crystal is a piezoelectric crystal.

Additional methods of forming LB films are known to those skilled in the art and are described in Ullman (1991) *An Introduction to Ultrathin Organic Films*, Academic Press, Boston, Mass.; and Roberts (1990) *Langmuir-Blodgett Films*, Plenum, N.Y.; the contents of which are incorporated herein by reference.

Once the PLSD is prepared by coupling the phage to the sensor, the signal output may be measured by any suitable device which is compatible with the crystal or sensor used to create the PLSD. Many such devices are known in the art and are commercially available. In some embodiments, measurements are carried out using a PM-740 Maxtek plating monitor with a frequency resolution of 0.5 Hz at 5 MGz. By “signal output” is intended any property of the sensor that changes in response to binding of a ligand and can be detected or monitored by a suitable device. Signal output of the device may be recorded and analyzed using a personal computer and appropriate data acquisition card and software. In some embodiments, the resonance frequency varies with the mass of the crystal as it changes due to interaction of ligands with the sensor. Because the voltage output from the Maxtek device is directly related to the resonance frequency of the quartz crystal sensor, changes in the resonance frequency and/or voltage may then be used to monitor the binding of ligand to the peptide of interest. The change in frequency and voltage will be proportional to the concentration of ligand, provided that nonspecific binding is sufficiently low. Once prepared, a PLSD may be used for multiple assays and may remain functional for a long period of time, up to a day, several days, a week, a month, several months, up to six months, a year, or more.

In methods and compositions for performing binding assays, it is desirable to have: (1) high surface density of landscape phage; (2) high specificity of interactions and a low level of non-specific binding; (3) accessibility of interacting partners; and (4) stability of the sensing system. PLSDs of the invention show improved properties over previously known devices, including a lower threshold of detection, increased strength of binding and greatly increased sensitivity. In addition, PLSDs exhibit the ability to bind very large particles, such as, for example, whole bacteria or spores or plant pollen. Under certain conditions, PLSDs also exhibit a synergistic effect of binding which contributes to the lower threshold of detection. While the invention is not bound by any particular mechanism of operation, these benefits are thought to derive from the multivalency of the phage, which can display up to 4,000 foreign peptides on the phage viral coat surface.

The PLSD is exposed to one or more ligands, typically by layering a solution that may contain a ligand onto the PLSD. PLSDs may also be exposed to gases. For example, PLSDs may be exposed to ambient air for the detection of harmful agents and toxins which are airborne contaminants such as spores of *Bacillus anthracis* (BAS). In other embodiments, solutions of purified or partially purified ligands may be exposed to the PLSD for quantitation or evaluation. Thus, any sample may be assayed by exposure to a PLSD, so long as the form of the sample is compatible with exposure to the PLSD. By purified or partially purified ligand solution is intended that the ligand used to make the solution is substantially free of cellular material and includes preparations of ligand having less than about 30%, 20%, 10%, 5%, 4%, 3%, 2%, or 1% (by weight) of contaminating material.

For detection of ligands, the PLSDs of the invention may be used in conjunction with device(s) that isolate and/or concentrate ligands from a sample. Thus, the PLSD may be configured with other devices to permit the continuous monitoring, detection and/or alarm of the presence of a particular ligand such as, for example, airborne anthrax spores (see Example 2).

In addition to providing assays for identifying ligands of foreign peptides, one of skill will recognize that the present invention has many applications. For example, the present invention provides assays and compositions for identifying solutions and compositions that do not interact with a particular foreign peptide. Thus, the present invention provides both positive and negative assays as well as quantitative binding assays which may be used in a variety of applications, for example, to design peptides or peptide moieties which may have particular properties. In this manner, ligands may also be compounds or compositions that may be useful because of their interaction or lack of interaction with the foreign peptide. For example, a ligand may be a pharmaceutical compound which binds to one foreign peptide but not to another, indicating that the pharmaceutical will bind to a cell surface marker of a particular cell type but not another.

The following examples are intended to illustrate, rather than to limit the invention.

EXPERIMENTAL

EXAMPLE 1

PLSDs for Detection of β-Galactosidase

β-galactosidase from *Escherichia coli* is a tetrameric protein of identical 1,023-residue polypeptides, with molecular dimensions of 17.5-13.5-9 nm. Phage that bind to this protein and to small haptens were isolated from phage display libraries as described in Petrenko and Smith (2000) *Prot. Eng.* 13: 589-592. Binding of phage to the antigen was confirmed by enzyme linked immunosorbent assay (ELISA) in which the phage were immobilized on the plastic surface of the ELISA wells and reacted with their antigens in solution (see Petrenko and Smith, id.). The phage was biotinylated using commercially available reagents and standard procedures (see, e.g., 2002 catalog from Pierce Biotechnology, Inc., Rockford, Ill.).

To prepare the sensor component of the device, AT-cut planar quartz crystals with a 5 MHz nominal oscillating frequency were purchased from Maxtek, Inc. Circular gold electrodes were deposited on both sides of the crystal sensor for the electrical connection to the oscillatory circuit. The microbalance and sensor were calibrated by the deposition of well characterized stearic acid monolayers. The deposition of an increasing number of stearic acid monolayers on the surface of a sensor resulted in a linear increase in mass. The deposition of a single monolayer of the stearic acid on the crystal sensor added an additional mass of $2.6\times10^{-7}$ g/cm$^2$ (for a 38 mNm$^{-1}$ transfer surface pressure). This value agreed well with the theoretical estimate based on the molecular area of the stearic monolayer in the condensed state. At this state, the area per molecule is ~20 Å$^2$ (for a single alkyl chain; see Ulman (1991), *An Introduction to Ultrathin Organic Films from Langmuir-Blodgett to Self-Assembly* (Academic Press, NY). The number of the stearic acid molecules in the monolayer of 1 cm$^2$ is $1\times10^{16}/20=5\times10^{14}$. The mass of one stearic acid molecule is 284 g/mole/$6.023\times10^{23}$ molecules/mole$=4.72\times10^{-22}$ g. The mass of the single monolayer should then equal $5\times10^{14}\times4.72\times10^{-22}$ g$=2.4\times10^{-7}$ g, which compares well with the obtained experimental value of $2.6\times10^{-7}$ g.

Figure 2:
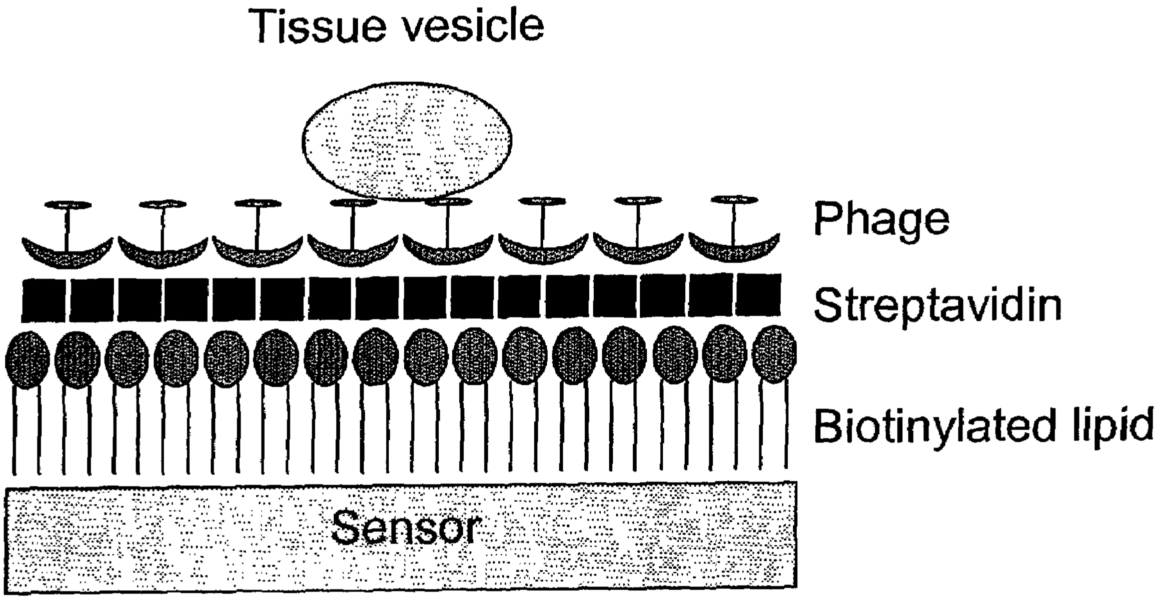
FIG. 2 shows a schematic design of an embodiment of the phage ligand sensor device (PLSD). The phage binding element is coupled to the sensor via a coupling composition layer comprising streptavidin. In the embodiment shown, a Langmuir-Blodgett film comprising biotinylated lipid has been deposited on the sensor. In addition, the landscape phage has been biotinylated. The addition of streptavidin results in molecular self-assembly whereby the landscape phage is coupled to the sensor.

To prepare the sensor to be coupled to the phage, monolayers containing phospholipid (N(biotinoyl)-1,2-dihexadecanoyl-sn-glycero-3-phosphoethanolamine) were transferred onto the gold surface of an acoustic wave sensor using the Langmuir-Blodgett technique to create a biotinylated sensor surface. Multilayers were obtained by successive dipping of the sensor through the monomolecular film deposited at a water-air interface. The phage was coupled with the phospholipid via streptavidin intermediates by molecular self-assembly to create a PLSD as diagrammed in FIG. 2.

Lipid monolayer depositions were carried out using a Langmuir-Blodgett (LB) film balance KSV 2200 LB (KSV-Chemicals, Finland). This fully computerized system contains a Wilhelmy-type surface balance (range 0-100 mN/m; sensitivity 0.05 mN/m), a Teflon trough (45×15 $cm^2$), a variable speed motor-driven Teflon barrier (0-200 mm/min), and a laminar flow hood. The trough was mounted on a 200 kg marble table. Vibration control was provided by interposing rubber shock absorbers, and by mounting the laminar flow hood on a separate bench. Surface pressure was monitored by use of a sandblasted platinum plate of 4 cm perimeter. The temperature of the aqueous subphase (20° C.±0.1° C.) was measured by a thermistor located just below the air/liquid interface and controlled by water circulation through a quartz tube coil on the bottom of the trough.

Lipid solutions were spread on the aqueous subphase as hexane solutions (1 mg/ml) containing 2% ethanol (Ito et al. (1989) *Thin Solid Films* 180: 1-13). The aqueous subphase used in the experiments was a solution containing 55 mM KCl, 4 mM NaCl, 0.1 mM $CaCl_2$, 1 mM $MgCl_2$ and 2 mM 3-(N-morpholino)-propanesulfonic acid (MOPS) made with deionized double distilled water (pH 7.4). After spreading, the monolayer was allowed to equilibrate and stabilize for 10 min at 19° C. The monolayer was then compressed at a rate of 30 mm/min and a vertical film deposition was carried out with a vertical rate of 4.5 mm/min and at a constant surface pressure of 25 mN/m. Eleven monolayers were transferred to the gold surface of the quartz crystals in this manner. Monolayers and multilayers deposited by LB technique were reasonably stable (see Pathirana et al. (2000) *Biosensors & Bioelectronics* 15: 135-141).

The PLSD was then assembled using the "molecular assembly" of biotin/streptavidin coupling. Streptavidin was added to immobilize the biotinylated phage on the sensor (covered with biotinylated lipids) as follows. The sensor was treated with subphase solution containing 0.01 mg/ml streptavidin for 2 hours, then rinsed with distilled water and dried for 2 minutes in ambient air. The sensor was then exposed to subphase solution containing biotinylated phage at 0.001 mg/ml for 2 hours and then rinsed and dried again as above. If necessary, these steps could be followed by a blocking step with a subphase solution containing biotin to prevent nonspecific binding of naturally biotinylated proteins to the sensor. Each prepared PLSD was then placed in an individual Petri dish and stored at 4° C. Tests described in this example were performed within 24 hours of assembling the PLSD.

Binding measurements were carried out using a PM-700 Maxtek plating monitor with a frequency resolution of 0.5 Hz at 5 MHz. Voltage output of the Maxtek device was recorded and records were analyzed offline. The voltage output from the Maxtek device is directly related to the resonance frequency of the quartz crystal sensor. Changes in the resonance frequency of the quartz crystal sensor were used to monitor the binding of β-galactosidase to the sensor surface. The observed changes are hypothesized to be due both to viscoelastic changes of the LB film near surface fluid media and the mass change associated with binding of the β-galactosidase.

For binding measurements, the PLSD was positioned in the probe arm of the instrument just before delivery of samples. Immediately after recording was started, 1000 μl PBS was delivered with a pipette to the PLSD surface and voltage was recorded for 4-8 minutes. Then PBS was removed carefully with a plastic pipette tip and a new recording was initiated. Different dilutions of β-Galactosidase in solution were added sequentially to the sensor and the same measuring procedure was followed after each addition. Each experiment was replicated 2-4 times, and the temperature of all samples was approximately 25° C. The data collected were stored and analyzed offline. The ratio of occupied (Y) and free (1−Y) phages on the sensor surface can be determined as $$\log(Y/(1-Y)) = \log K_b + n \log [C] \quad [1]$$

where $K_b$ is the association binding constant, C is a β-galactosidase concentration, and n is the number of molecules bound to a single phage. A plot of the left-hand side of equation (1) versus log[C] is known as a Hill plot (see Kuchel & Ralston (1988) *Theory and Problems of Biochemistry* (McGraw-Hill, New York)). A Hill plot gives an estimate of n from the slope, $K_b$ from the ordinate intercept, and $EC_{50}$ at the point when Y=1−Y.

Figure 3:
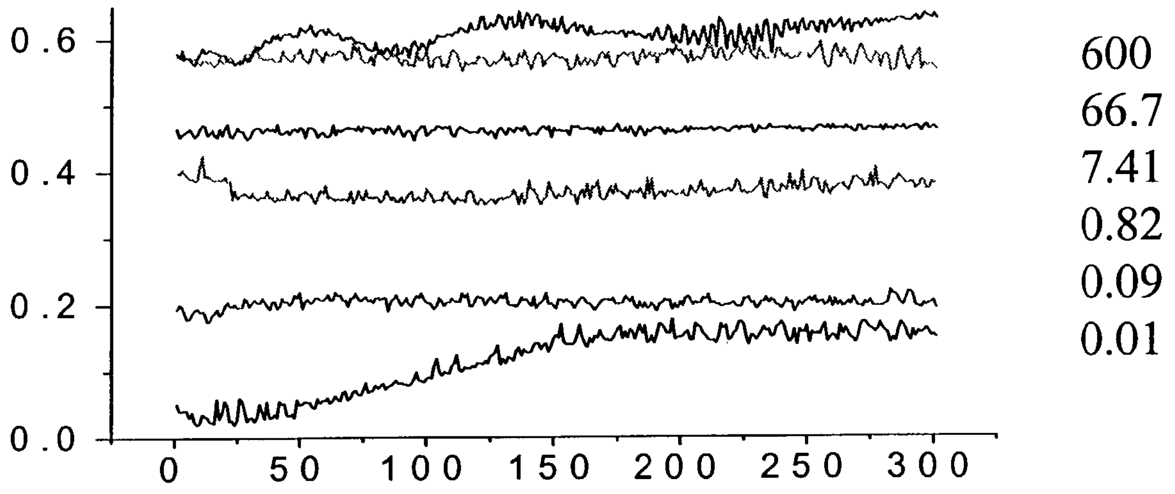
FIG. 3 shows a typical response curve obtained from a PLSD sensor. In this particular example, the binding element of the PLSD comprised phage that were affinity-selected by binding to β-galactosidase (see Example 1). The PLSD was then exposed to different concentrations of β-galactosidase in PBS. PBS with no β-galactosidase was used as a reference. The response of the sensor, measured in Volts, is shown as a function of time. Each line represents data points taken once a second during exposure of the sensor to the solution. Response (in Volts) is shown on the left vertical axis as a function of time (in seconds) on the horizontal axis; numbers on the right indicate β-galactosidase concentration (nanomolar) corresponding to each line.

Data obtained from the binding measurements are shown in FIG. 3. As described above, these data were obtained by exposing the sensor to β-galactosidase solutions of different concentrations. The sequential application of β-galactosidase solutions, beginning with the most dilute and ending with the most concentrated, showed elevations of voltage with each application, indicating that additional material was binding to the PLSD. For each β-galactosidase concentration, the sensor signal approached a steady-state value corresponding to that concentration within 100 seconds or less. The response curves are distinguished by the fast reaction time, the attainment of a steady state, and low non-specific binding.

Figure 4:
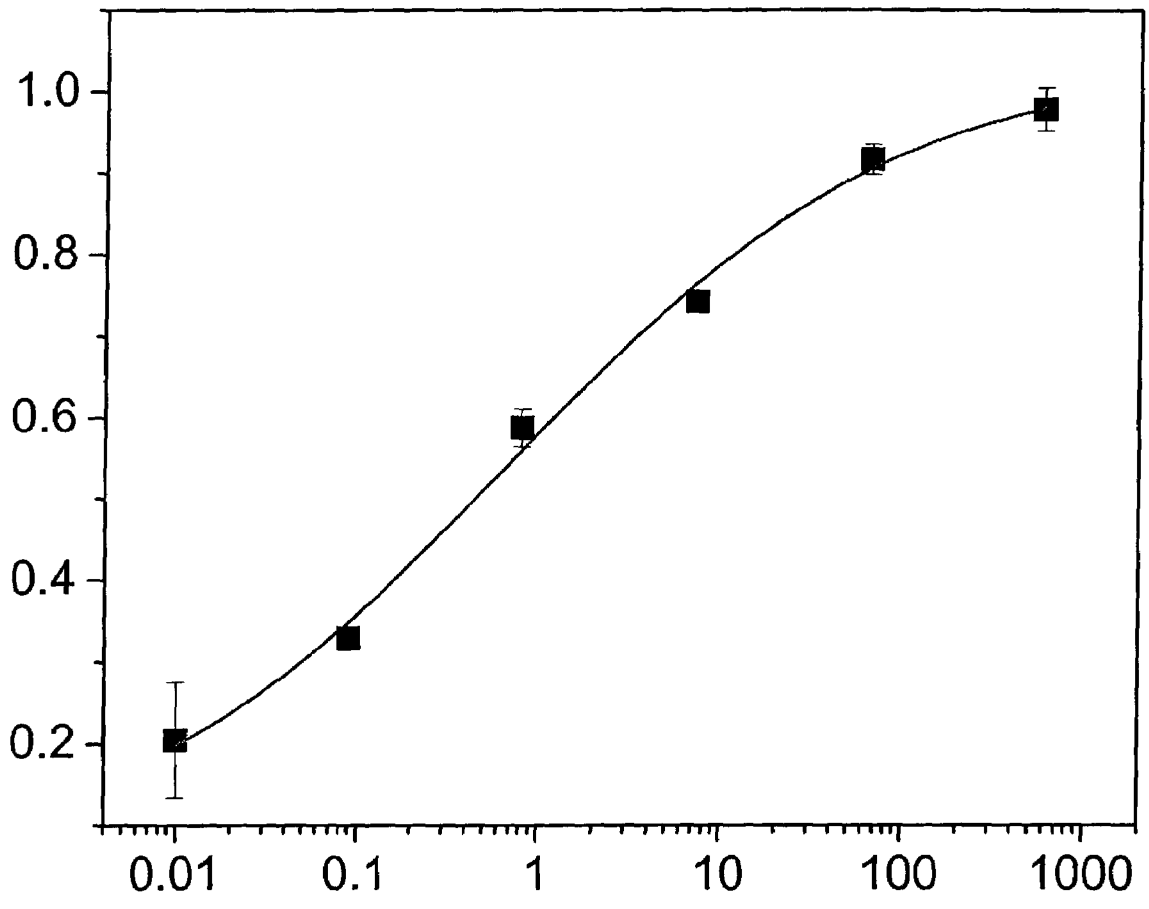
FIG. 4 shows a dose-response plot of the steady state output sensor voltages from the PLSD of Example 1 as a function of the relative concentration of β-galactosidase (nanomolar). Black squares represent the mean values of steady-state output sensor voltages; bars represent standard deviation (S.D.). Experimental values were obtained by averaging about 200 data points of each steady-state level of response curves (as exemplified in FIG. 3) and corrected for the mean value of the voltage response to PBS without β-galactosidase. Smooth curves are the sigmoid fits to the experimental data ($X^2$=0.199, $R^2$=0.99).
Figure 5:
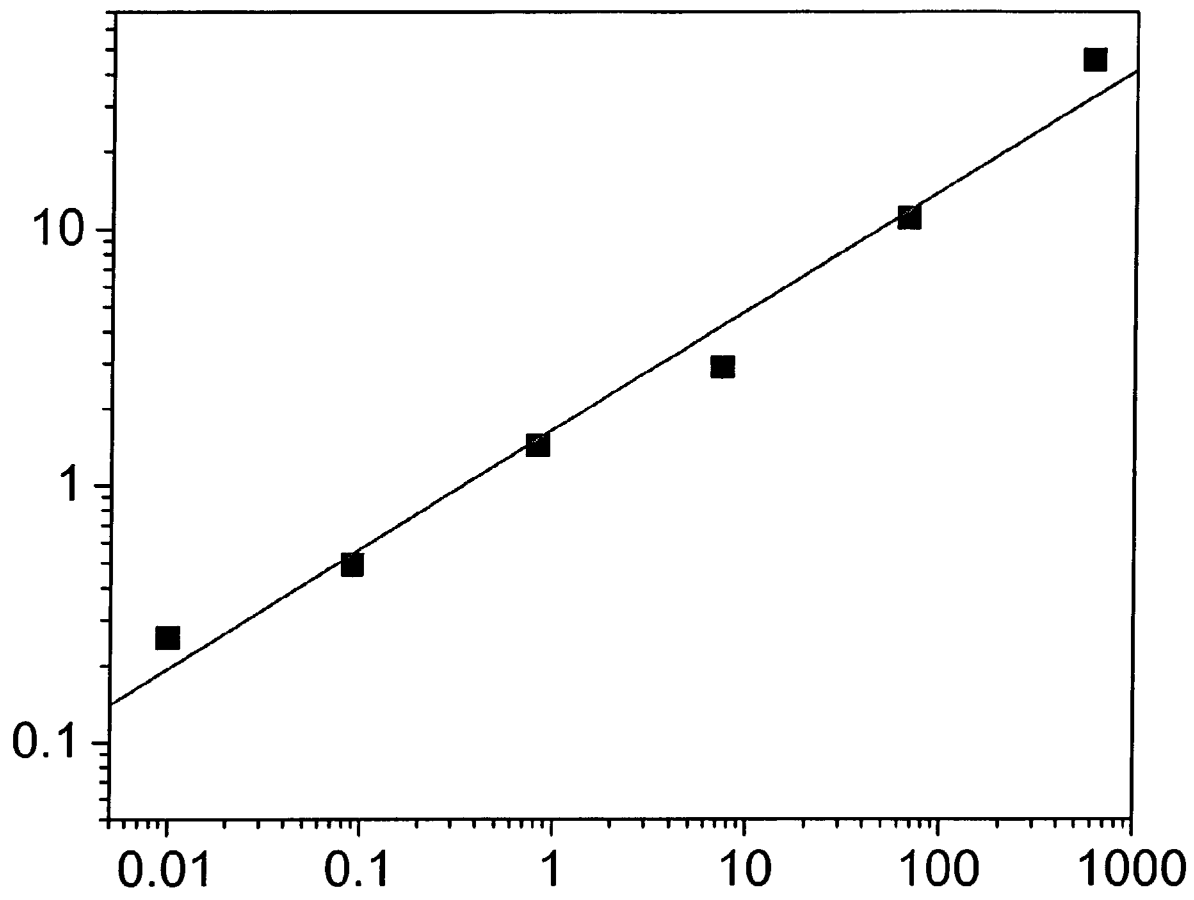
FIG. 5 shows a Hill plot (see Example 1). The ratio of occupied and free β-galactosidase molecules on the sensor surface is shown as a function of β-galactosidase concentration (nanoMolar). The black squares represent experimental data, and the line represents the least square fit of equation [1]. The Hill coefficient was 2.1, and the $K_D$ was 1.7 nanoMolar.

FIG. 4 depicts the mean values of the steady state output sensor voltages from the PLSD plotted as a function of the relative concentration of the β-galactosidase. The binding dose response curve had a typical sigmoid shape and the signal was saturated at a β-galactosidase concentration of about 600 nM. The corresponding Hill plot is shown in FIG. 5. Binding parameters calculated from the Hill plot equation were as follows: Hill coefficient, 2.1±0.1; Dissociation constant, 1.7±0.5 nM; Maximal Response, 0.65±0.19; Maximal binding, 130±30 $Ng/cm^2$.

Another embodiment of the invention provides an improved sensor platform that is a surface plasmon resonance (SPR) sensor. SPR sensors are recognized tools in biorecognition characterization (Malmborg and Ohlin (1999) *Int'l. J. of Bio-Chromatography* 4: 163-173). A PLSD was constructed using phage selected against β-galactosidase as the binding element and an SPR sensor. This PLSD demonstrated strong binding to β-galactosidase (FIG.

10). This SPR technique could be optimized to monitor real-time binding of *B. anthracis* spores to phage in a flow of liquid (see, e.g., Example 6).

EXAMPLE 2

Construction of Engineered Phage Libraries

A large ($10^9$-clone) phage library was constructed by splicing a degenerate coding sequence into the beginning of the pVIII coat-protein gene, replacing wild-type codons 2-4 (Petrenko et al. (1996) *Protein Engineering* 9: 797-801). The degenerate coding sequence used is underlined below in Table 1:

TABLE 1

Sequence Used to Generate Phage Library

DNA
GCA<u>GNKNNKNNKNNKNNKNNKNNKNN</u>GGATCCCGCAAAAGCGGCCTTTGACTCC    (SEQ ID NO:1)

pVIII amino acid sequence
| A | X | X | X | X | X | X | X | X | D | P | A | K | A | A | F | D | S | (SEQ ID NO:2) |
|---|---|---|---|---|---|---|---|---|---|---|---|---|---|---|---|---|---|---|
| 1 |   |   |   |   |   |   |   |   | 5 | 6 | 7 | 8 | 9 | 10| 11| 12| 13|   |

In the DNA sequence, each N represents an equal frequency of all four nucleotides (A, G, C and T), while K represents an equal frequency of G and T. As a result of this modification, every pVIII subunit in an engineered phage was five amino acids longer than the wild-type pVIII subunit and displayed a "random" sequence of eight amino acids, or an octamer ($X_8$ above). In any single clone, the random octamer was the same in every particle, but almost every clone displayed a different random octamer. The octamers are thought to be arranged regularly around the outside of the virion, occupying a substantial fraction of the surface.

Figure 6:
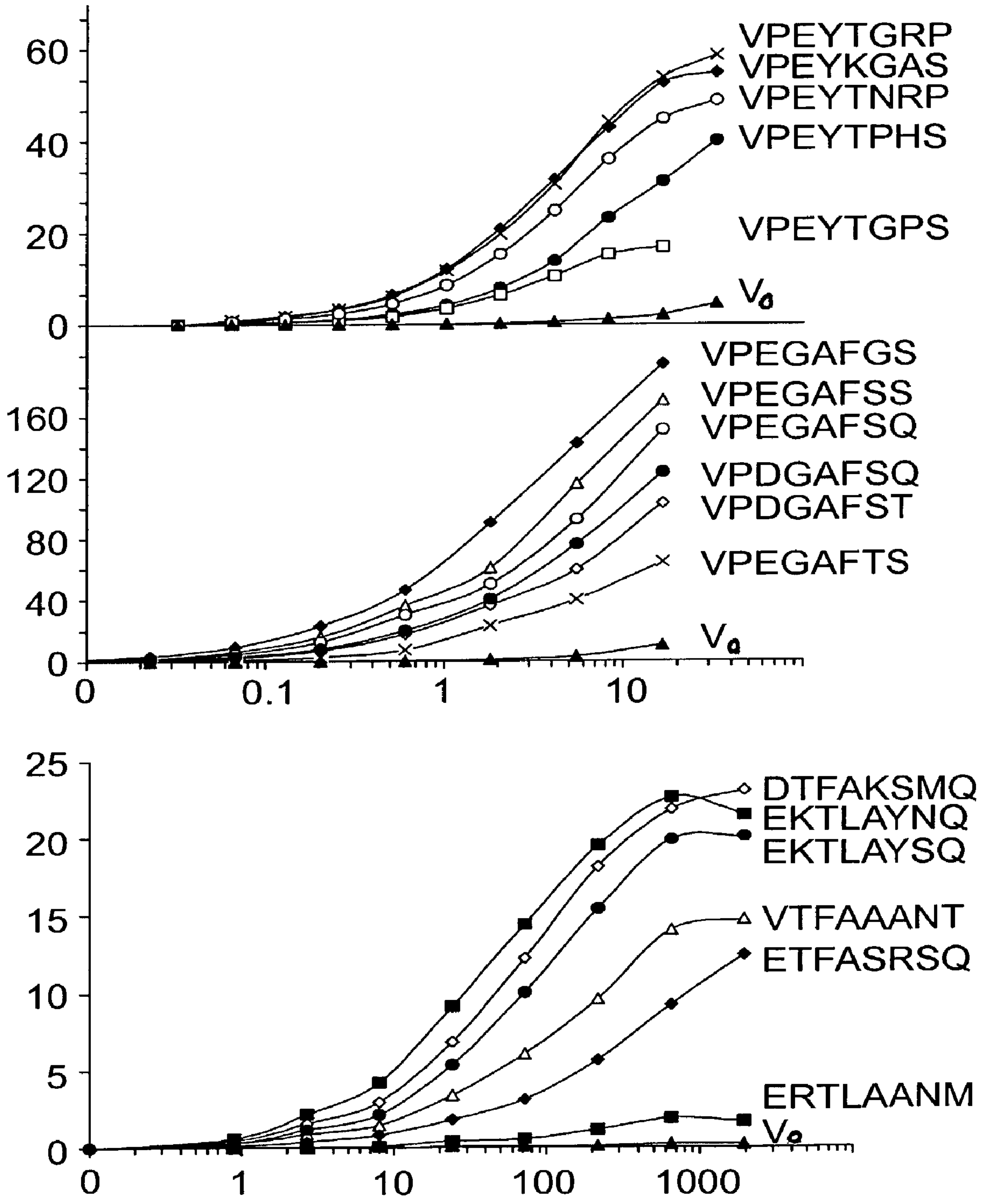
FIG. 6 shows ELISA results in which three model ligands (alkaline phosphatase-labeled neutravidin and streptavidin, and unlabeled β-galactosidase) were reacted directly with immobilized, peptide-bearing phage; the data demonstrate specific dose-dependent binding of each antigen to the peptides it selected (see Example 3). Each binding curve is labeled with the altered amino acid sequence of the foreign peptide carried by the phage being tested ($V_o$=vector control). ELISA signal (mOD/min) is shown as a function of ligand concentration (micrograms/ml for top two panels; nanomolar for bottom panel). The top panel shows results for phage isolated with the ligand neutravidin; the middle panel shows results for phage isolated with the ligand streptavidin; and the bottom panel shows results for phage isolated with the ligand β-galactosidase.

Another library was constructed using random nonamers (9-mers). In this library, the aspartic acid D in position 5 of major coat protein (see Table 1) was also deleted and the deleted region was substituted with random nonamers. In addition, an f8-alpha library was constructed which contained $10^8$ clones. In this library, the major coat protein pVIII had random amino acids substituted in positions 12-13, 15-17 and 19 of the pVIII protein, as shown below in Table 2:

*Escherichia coli*). Each protein was absorbed to the surface of a 35-mm polystyrene Petri dish and exposed to the phage library. Unbound phage were washed away, and bound phage was eluted with acid buffer and amplified by infecting fresh bacterial host cells. After three rounds of selection, individual phage clones were propagated and partially sequenced to determine the amino acid sequence of the displayed foreign peptide. The selected phage were further characterized by enzyme linked immuno sorbent assay (ELISA) in which the phage were immobilized on the plastic surface of ELISA wells and reacted with the ligands in solution phase. Neutravidin and streptavidin were labeled with alkaline phosphatase, while β-galactosidase was unlabeled. The data (graphed in FIG. 6) demonstrate specific dose-dependent binding of each ligand to the peptides it selected. Inhibition ELISAs verified that non-immobilized peptide-bearing phage compete with immobilized phage for binding to their respective ligands.

Sequence analysis of the selected phage revealed "motifs," or consensus sequences of foreign peptides displayed by phage to which the ligand would bind. The strepavidin-binding motif VP(E/D)(G/S)AFXX (where 60% of X is S or T) (SEQ ID NO:4) is strikingly similar to the neutravidin-binding motif VPE(F/Y)XXXX (where 34% X are S and T) (SEQ ID NO:5). However, binding was shown to be strongly species specific: phage selected with streptavidin did not bind neutravidin and vice versa. Two different groups of foreign peptides were displayed on β-galactosidase-binding phage, with consensus motifs EKTLAYXQ (SEQ ID NO:6) and (D/E)TFA(KIRIx)XXX (SEQ ID NO:7; where the position marked (K/R/x) has >50% basic K and R residues). Phages from these two groups competed with each other for binding to β-galactosidase, and therefore probably bind nearby sites on the ligand.

TABLE 2

Sequence Used to Generate f8-alpha Phage Library

| 1 | 2 | 3 | 4 | 5 | 6 | 7 | 8 | 9 | 10 | 11 | **12** | **13** | 14 | **15** | **16** | **17** | 18 | **19** | 20 | 21 | 22 | 23 | 24 | (SEQ ID NO:3) |
|---|---|---|---|---|---|---|---|---|----|----|--------|--------|----|--------|--------|--------|----|--------|----|----|----|----|----|---|
| A | E | G | E | D | P | A | K | A | A  | F  | **X**  | **X**  | L  | **X**  | **X**  | **X**  | A  | **X**  | E  | Y  | I  | G  | Y  |   |

where X stands for any amino acid. As indicated by the creation of these libraries, one of skill can readily design and create a variety of phage libraries with randomized foreign peptides.

EXAMPLE 3

Selection of Phage that Bind Particular Lilands

Model ligands selected for creating PLSDs were: streptavidin (from the bacterium *Streptomyces avidinii*), avidin (from chicken egg white) and β-galactosidase (from Selection of Phage that Bind *Bacillus anthracis* Spores A veterinary vaccine strain variant of *Bacillus anthracis* (strain "Steme") was obtained. Spore-binding phage were selected from a phage library in which each of approximately a billion clones had unique random octamer peptides fused to the major coat protein pVIII on the surface of phage (Petrenko et al. (1996) *Protein Engineering* 9: 797-801; Petrenko et al. (2000) *Protein Engineering* 13: 589-592).

Two different schemes of affinity selection were used. In the first, spore-binding phage were precipitated by centrifugation, washed, and eluted with mild acid and infected *E. coli* cells. Infected cells were grown in media containing tetracycline and kanamycin—antibiotics that kill *B. anthracis* but will not kill phage-infected *Escherichia coli* cells. This sub-group of phage was amplified and used in the next round of selection. After four rounds of amplification and selection, the phages were eluted and propagated as isolated clones. Phage DNA was then sequenced to determine the structure of the foreign peptides:

TABLE 3

Selected foreign peptide motifs

| Selected by co-precipitation with spores | | Selected by affinity-sorption to immobilized spores | |
|---|---|---|---|
| DPRTVSTA (7) | SEQ ID NO:8) | EPRAPASL | SEQ ID NO:18) |
| DRTSSNTT (11) | SEQ ID NO:9) | EPRLSPHS | SEQ ID NO:19) |
| DRSASSTA (2) | SEQ ID NO:10) | EPKPHTFS (4) | SEQ ID NO:20) |
| DRTSQNLQ (2) | SEQ ID NO:11) | EPHPKTST | SEQ ID NO:21) |
| DRSGTSPS | SEQ ID NO:12) | ETRVPHGA | SEQ ID NO:22) |
| DRNVNGPS | SEQ ID NO:13) | DARGTTHM | SEQ ID NO:23) |
| ERGSNATL | SEQ ID NO:14) | EKTPVTAT (2) | SEQ ID NO:24) |
| DSRNEKSM (3) | SEQ ID NO:15) | ERTVATTQ | SEQ ID NO:25) |
| ESRNSPAA | SEQ ID NO:16) | VTRNTSAS | SEQ ID NO:26) |
| VMDRTQPP | SEQ ID NO:17) | VSQPASPS | SEQ ID NO:27) |
| | | ESFSAYSG | SEQ ID NO:28) |

To verify that the selected phage bound to spores, a binding assay was performed in which $10^9$ cfu (colony-forming units) of each phage clone were individually mixed with $10^8$ *B. anthracis* spores. Pellets were washed and eluted with acid as described above, and phage recovery was measured. Recoveries of different clones ranged from 20-29%, in contrast to control levels of recovery around 3% in the absence of spores. However, a recovery control using phage unrelated to the selection experiment showed a level of recovery over 4 logs lower. These results demonstrate that phage selection by coprecipitation with spores selected phage that bind spores and also phage that tend to precipitate by centrifugation.

To increase binding specificity in the selection procedure, another protocol was used. This protocol is based on affinity sorption of phage to immobilized spores. In this protocol, the phage library was incubated with spores immobilized onto the wells of microtiter dish. Unbound phage were washed away, and bound phage were cluted with mild acid and propagated in bacterial cells. After four rounds of selection, phages from the final sub-library were propagated as individual clones and sequenced. Foreign peptides selected in this protocol are presented in Table 3. These peptides differ from peptides isolated in the co-precipitation protocol, having some common features at their N-terminus.

Phage-capture ELISA was then used for additional screening of the spore-binding candidate phages. In this assay, spores were immobilized onto wells-of a microtiter dish and reacted with the selected phage candidates. After extensive washing of the dish, bound phages were quantitated via consecutive reactions with biotinylated anti-phage antibodies, alkaline phosphatase-streptavidin conjugate (APSA) and p-nitrophenyl phosphate (PNPP). The kinetic of the color reaction was measured using a Bio-Tek reader. The results showed that about half of the selected clones give consistently higher signals than control wild-type phage.

Figure 7:
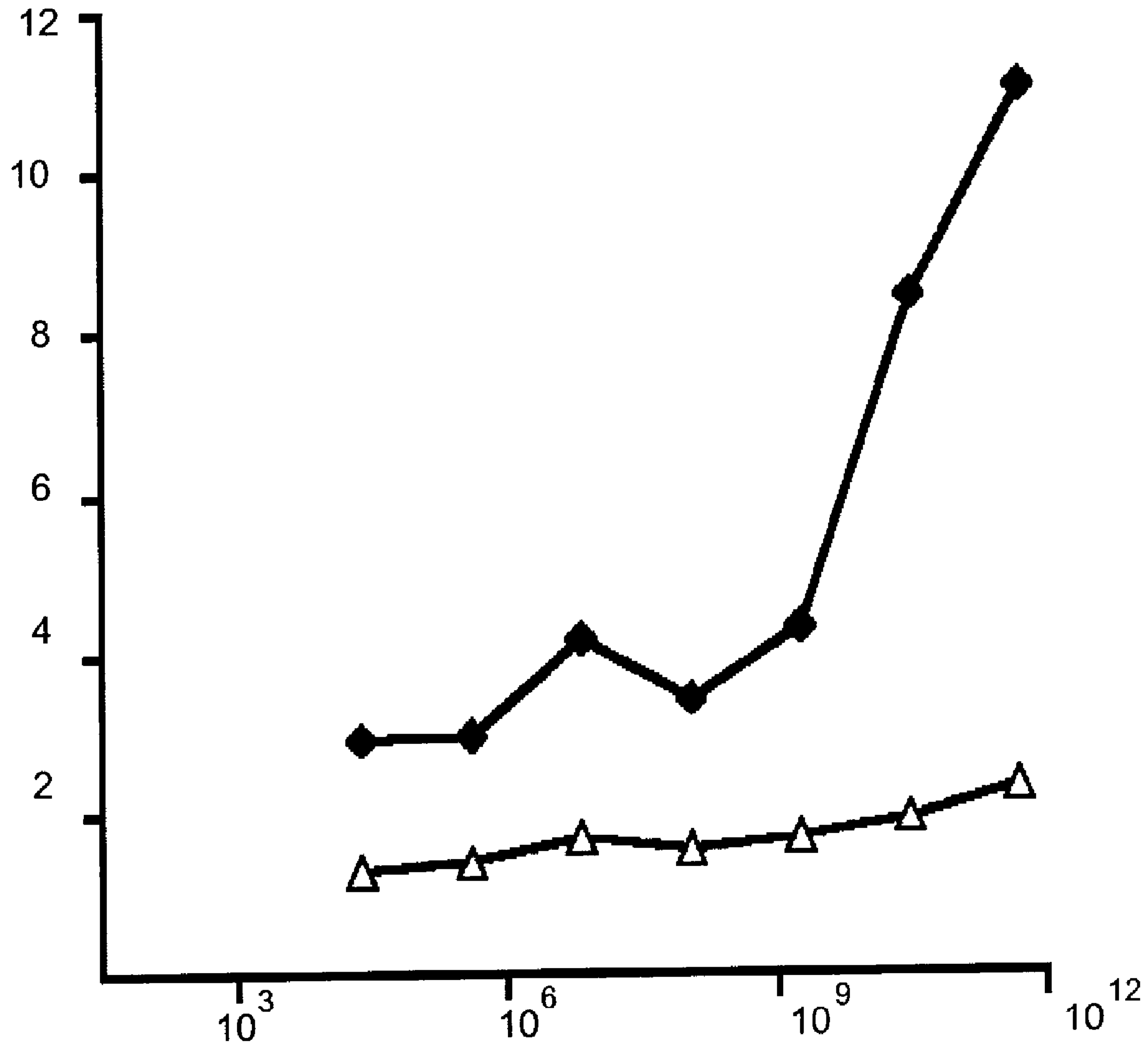
FIG. 7 shows direct ELISA results for detection of spores with one of the selected phage clones (see Example 3). ELISA signal (mOD/min) is shown as a function of *B. anthracis* spore concentration (particles/ml). The difference in binding profiles of the selected phage clone (black diamonds) and control vector phage f8-5 (open triangles) demonstrates a high specificity of interaction.

The most promising phage candidates were further characterized by direct ELISA, in which the phages were immobilized to wells of a microtiter dish and reacted with the spores in solution. The spores bound to the phages were detected with consecutive reactions with anti-*B. anthracis* spore monoclonal antibodies, goat anti-mouse antibodies conjugated with alkaline phosphatase and PNPP. FIG. 7 shows detection of the spores with one of the selected clones using the ELISA. The difference in binding profiles of the selected clone and control vector phage f8-5 reflects a high specificity of their interaction with *B. anthracis* spores.

Figure 8:
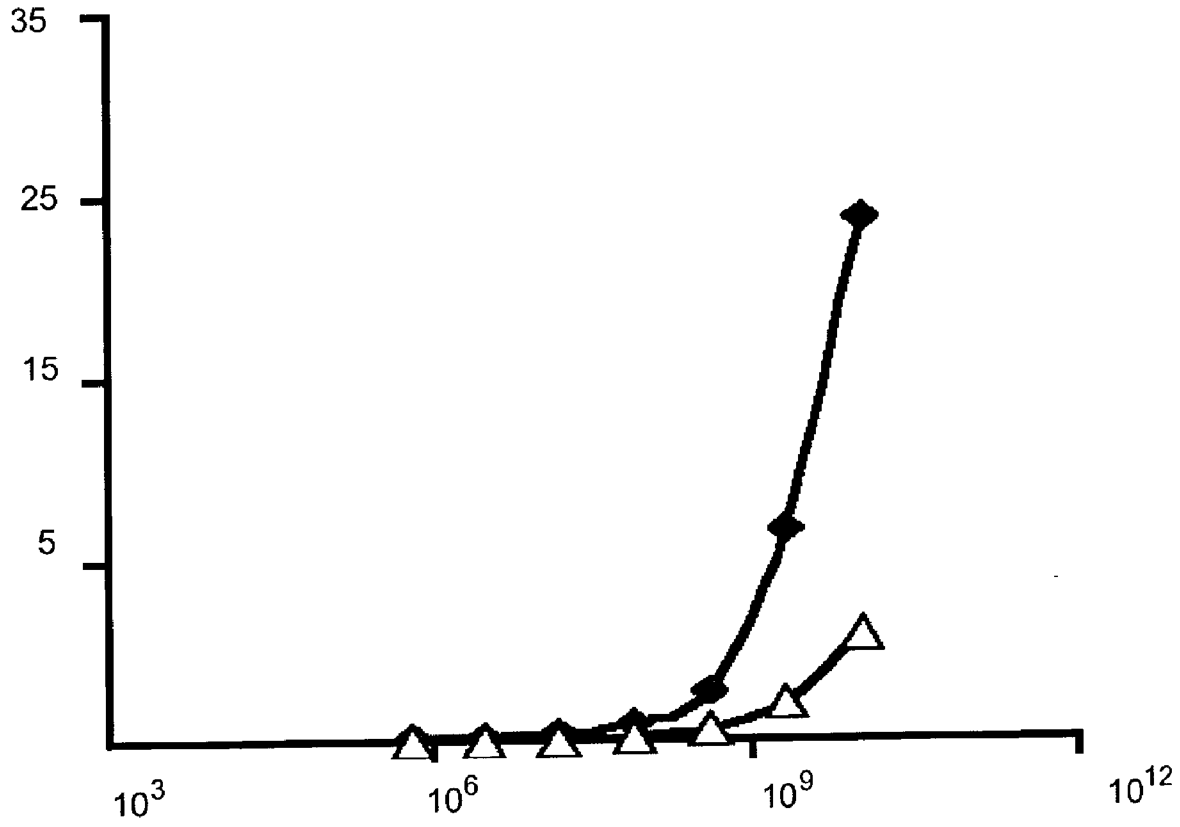
FIG. 8 shows the results of a different ELISA format to evaluate the selected phage (see Example 3). ELISA signal (mOD/min) is shown as a function of biotinylated spore concentration (particles/ml). As seen for the experiment shown in FIG. 7, the difference in binding profiles of the selected phage clone (black diamonds) and control vector phage f8-5 (open triangles) demonstrates a high specificity of interaction.

To study selectivity of phage-derived probes, an ELISA format was utilized in which the complex sandwich of spores/anti-spore antibody/anti-mouse antibody is replaced by biotinylated spores. The spores were biotinylated with EZ-Link-™ Sulfo-NHS-LC-Biotin (Pierce Biotechnology, Inc., Rockford, Ill.), extensively washed, and incubated with phage probes that were immobilized onto the wells of a microtiter dish. Spore-phage complexes were detected by reaction with alkaline phosphatase conjugated with streptavidin (APSA) and p-nitro-phenyl phosphate (PNPP). Results are shown in FIG. 8.

EXAMPLE 4

PLSDs Exhibit Higher Binding Constants than Comparable ELISAs

A thickness shear mode (TSM) quartz acoustic wave sensor (reviewed in Ivnitski et al. (1999) *Biosensors & Bioelectronics* 14: 599-624) was selected for the sensor component of a PLSD for the detection of β-galactosidase. Monolayers containing biotinylated phospholipid were transferred onto the gold surface of the acoustic wave sensor using the Langmuir-Blodgett technique. Biotinylated phage was coupled with the phospholipid layer via streptavidin intermediates by molecular self-assembly to create the PLSD. Experiments were carried out using a TM-400 Maxtek thickness monitor with a frequency resolution of 0.05 Hz at 5 MHz.

Experiments comparing the dose-dependent binding of β-galactosidase to phage immobilized to an ELISA plate and to the PLSD showed that affinity of the complex depended on the mode of phage immobilization and type of analytical platform: 30 nM in ELISA and 0.6 nM in TSM quartz sensor (see FIG. 9A). The dissociation constant of 0.6 mM compared well with one found for antibodies isolated from a phage display library (Vaughan et al. (1996) *Nat Biotechnol.* 14:309-14). The difference in affinities can be attributed to the monovalent (ELISA) versus divalent (PLSD) interaction of the phage with β-galactosidase, as indicated by Hill-presentation of binding curves (FIG. 9B; Connors (1987) *Binding Constants: The Measurements of Molecular Complex Stability* (John Wiley & Sons, New York). Binding of the phage was quite specific because the response was reduced by 85% if β-galactosidase was preincubated with $2.2\times10^{12}$ vir/ml of free phage. Binding of the phage to β-galactosidase was also very selective because the presence of 1000-fold excess of bovine serum albumin (BSA) in the incubation solution with the β-galactosidase did not considerably change the signal in the ELISA and reduced the PLSD signal only by 40%.

EXAMPLE 5

Rapid Production of Affinity-Selected PLSDs

The PLSDs of the invention can readily be produced to detect target ligands, such as, for example, target receptors and biological threat agents (see, e.g., Smith and Petrenko (1997) *Chemical Rev.* 97: 391-410). Phage that bind specifically to particular bacterial species ("species-specific" phage) are selected from different phage-display libraries with repertoires of displayed peptides (see, e.g., Petrenko et al. (1996) *Protein Engineering* 9: 797-801; Kouzmitcheva et al. (2001) *Clinical & Diagnostic Laboratory Immunology* 8: 150-160). Primary candidate phage-probes are obtained and screened by ELISA to find the best candidates with highest affinity and selectivity. If necessary, clones with enhanced affinity and selectivity are selected from "secondary" phage libraries prepared by mutagenesis of primary candidate phage-binders or by shuffling with a new landscape library. Shuffling is a technique well-known in the art. See, e.g., Minshull and Stemmer (1999) *Current Opinion in Chemical Biology* 3:284-290; Christians et al. (1999) *Nature Biotechnology* 17: 259-264.

Non-virulent strains of pathogenic bacteria may be used in selecting the phage. For example, *Bacillus anthracis* Sterne, a virulent veterinary vaccine strain, does not contain plasmid pXO2, which carries the genes required for capsule production in vegetative cells, but has all antigenic markers common with pathogenic *B. anthracis* strains. It can kill certain strains of mice (e.g., A/J mice) but does not harm humans and most other mammals. Phage probes and sensors may be tested against pathogenic *B. anthracis* Aim strain in appropriate facilities (e.g., BSL3).

Affinity Selection

Immobilized BAS (*B. anthracis* spores) are incubated with a portion of the phage library containing about $10^{11}$ virions (about 100 particles of each phage clone will be present in the mixture). Unbound phage from libraries is washed away, and bound phage is eluted with mild acid. Each round of selection enriches the portion of BAS-binders in the phage population 100-1000 times. Multiple rounds of selection are performed while monitoring the enrichment of the phage population calculated as a ratio of "incoming" phages to "outcoming" (i.e., selected or eluted) phages. Usually, affinity selection leads to isolation of 0.1-1% of binding phages. Ninety-six clones of selected phages from each library (total number about 1000) are propagated and tested for binding to BAS by ELISA.

Screening for BAS-Binding Phage

Binding phage clones are initially characterized using phage-capture ELISA. BAS (*B. anthracis* spores) are absorbed on the wells of microtiter dishes. Phage clones are propagated in the *E. coli* host bacterium K91BK and, after separation of cells by centrifugation, used without concentrating as a supernatant suspension to cover the immobilized BAS. After the plate is washed, biotinylated anti-phage IgG is loaded into the wells. Ultimately, binding phage are identified by adding to the washed wells a conjugate of alkaline phosphatase with streptavidin (APSA) and, after incubation and extensive washing, the chromogenic substrate of AP-o-nitrophenylphosphate. Plates are washed on an ELX405 washer and the kinetics of increase of optical density are determined on an ELISA reader EL808 (BioTek).

Candidate phages, identified by phage-capture ELISA, are propagated in 20 ml of infected bacteria, purified and tested as potential probes in indirect ELISA. In this reversed format, the capture phage are immobilized to the wells, and mouse anti-BAS antibodies can be used to detect the bound species. Ultimately, bound species are confirmed with rabbit anti-mouse IgG antibodies conjugated with alkaline phosphatase.

Selectivity of phage may be evaluated by reacting biotinylated *B. anthracis* spores with the phage in direct ELISA format with and without non-biotinylated spores of another bacterial species (e.g., *Bacillus subtilis, Bacillus globigii*, etc.). If the tested phage is not selective for BAS, the ELISA signal drops due to competition of biotinylated and non-biotinylated probes. If the ELISA signal does not change in the presence of non-BAS spores, the interaction of the phage with BAS is considered selective. The phage binders are propagated in 4-liter scale, purified and used as probes in the biosensors.

One of skill in the art will appreciate that the affinity and selectivity of target binding by a particular phage can be enhanced by techniques routine in the art, such as mutagenesis and screening for phages with improved properties. One method for obtaining phage with improved binding properties involves mixing selected primary candidates with a new landscape library and co-infecting into bacterial *E. coli* cells to obtain a collection of phage covered with a mixture of primary lead-peptide and random peptide gained from the new library. For selection of improved phage, the new library contains phage harboring a chloramphenicol resistance gene. Recombinant phage are obtained from cells growing in presence of both tetracycline and chloramphenicol. This "secondary" library is a rich source of phage with potentially better binding properties.

In another approach, affinity-selected phage are extensively mutagenized using a modified Kunkel method (see Kunkel et al. (1987); Weiss et al. (2000)), which may be performed on a sub-portion of the foreign peptide. *E. coli* cells are transformed with the mixture of mutated DNA to obtain a new "sub-library" with a new repertoire of peptides. This sub-library is used for selection of phage that have better binding properties under more stringent conditions. Essentially, this "phage maturation" process mimics the efficient natural process of maturation of antibodies, increasing their affinity by orders of magnitude.

It may happen that the phage binders are selected against a spore ligand that is common to different species of *Bacillus*. To isolate more selective phage probes directed against species-specific ligands of *B. anthracis*, various approaches may be employed, including approaches such as library depletion and receptor blocking. In the library-depletion approach, the phage library is screened against spores of *Bacillus* species that can cross-react with phage that bind to *B. anthracis*, and "non-selective" phage that cross-react with different *Bacillus* species are separated from the library. After separation of cross-reacting phage, the rest of the library is used for selection of phage that bind to *B. anthracis*, as described above.

In the receptor blocking approach, affinity-selected phages are reconstructed to delete their tetracycline resistance gene. These phage, which are missing the $Tet^R$ marker, will block their ligand and are mixed with the library in order to block the ligand when the library is exposed to the target ligand. The altered phage are infective but cannot support growth of *E. coli* cells in medium containing tetracycline, while clones from the library will be able to support growth in tetracycline-containing medium. Using this strategy, phage clones are selected that target new, alternative receptors on the spores. Alternation of selection and blocking steps can be used to isolate probes that recognize different receptors on the spores.

EXAMPLE 6

Detection of Airborne Contaminants

A PLSD is configured with another device to allow for the continuous monitoring of an air sample for the presence of *Bacillus anthracis* ("anthrax") spores. While PLSDs may be used to evaluate an air or gas sample, combination of a PLSD with other devices to create a sensing system may enhance the sensitivity of detection.

A SpinCon® air-to-liquid concentrator (Sceptor Industries, Inc., Kansas City, Mo.; also see Cage et al. (1996) *Annals of Allergy, Asthma, & Immunology* 77: 401-406) separates particulate matter from air and traps the particulate matter in a liquid stream. The SpinCon® output stream is typically analyzed with assays such as PCR and cell culture, but to create a sensing system, the SpinCon® device is configured so that fluid from the SpinCon® is directed across the surface of the PLSD and continuously monitored for the presence of anthrax spores. This configuration of the SpinCon® with the PLSD of the invention provides continuous, real-time monitoring of an air sample.

The PLSD comprises a binding element of phage that is selected from a phage library for ability to bind to anthrax spores. These phage are improved for use in the PLSD with mutagenesis and affinity maturation as described elsewhere herein. The phage demonstrating the best binding to anthrax spores in an Enzyme Linked Immunosorbent Assay (ELISA) are engineered to eliminate their *Esherichia coli*-binding domains and are then used to create a PLSD. Phage are immobilized onto the surface of either a miniaturized plasmon surface resonance or acoustic wave resonator. Specificity and selectivity of detection of anthrax spores are evaluated using anthrax spores mixed with unrelated spores, proteins and other biopolymers.

EXAMPLE 7

Production of Customized PLSDs

The Langmuir-Blodgett (LB) technique is used as a method of immobilization of phage to the acoustic wave sensor. LB films provide precise control of the film thickness and the molecular architecture that is deposited and preserve the sensitivity and specific recognition properties of molecules (Pathirana et al. (2000) *Biosensors & Bioelectronics* 15: 135-41; see also co-pending U.S. application Ser. No. 09/452,968, filed Dec. 2, 1999, herein incorporated in its entirety by reference).

Candidate phage are remodeled or engineered to remove the *E. coli*-binding site and introduce an in vivo biotinylation site (Beckett et al., 1999). Phage are biotinylated in vivo and/or in vitro and immobilized to the sensor using biotin/streptavidin coupling. Phage biotinylated in vivo are biotinylated on their tip, while phage biotinylated in vitro have many biotin residues distributed randomly along the body of the particle. Alternatively, phage are deposited directly onto the gold surface of the sensor. By selecting a particular method of biotinylation and controlling the density of phage on the sensor, phage arrays may be assembled that have optimal properties for the assay of interest. Binding elements comprising very dense, linear phage arrays ("velvet-type" array) tend to exhibit monovalent binding behavior, while less-dense, non-linear phage arrays ("felt-type" array) tend to exhibit multivalent binding behavior.

The non-infective mutant fKN16 of the phage fdtet has been shown to provide a high yield of phage particles from *E. coli* culture (Nelson et al. (1981) *Virology* 108:338-50.) The fnKN16 mutation is a deletion of domains D1-D2 in the minor coat protein pIII. A DNA fragment encoding the wildtype or nonaltered domain D3 from phage fKN16 is transferred into DNA of the selected phage using available restriction sites and conventional cloning techniques. A peptide biotinylation substrate (Beckett et al. (1999) *Protein Science* 8: 921-929) is then introduced into the modified pIII gene using site-directed mutagenesis.

Phage are immobilized onto the gold surface of biosensors using techniques known in the art. In one approach, the sensor is covered consecutively with biotinylated LB film, streptavidin, and biotinylated phage, allowing the phage to adopt varying tertiary conformations, thus forming arrays that range from pure "felt-type" to pure "velvet type." Biotinylated phage may also be immobilized on a neutravidin-coated gold sensor surface. The conformation of phage may be confirmed with scanning electron and atomic force microscopy (see also co-pending U.S. application Ser. No. 09/452,968, filed Dec. 2, 1999).

Acoustic wave device (AWD) measurements are carried out using a PM-740 Maxtek plating monitor with a frequency resolution of 0.05 Hz at 5 MHz. Voltage output, which is directly related to the resonance frequency of the quartz crystal sensor, is recorded and analyzed offline. Changes in the resonance frequency of the quartz crystal sensor indicate the binding of the analyte to the sensor surface. Any appropriate sensor may be used for surface plasmon resonance (SPR) measurements, such as, for example, the Spreeta™ sensor (Texas Instruments, Dallas, Tex.), a miniature, fully integrated SPR device provided with a small flow cell. Specificity and selectivity of detection of ligands may be examined; for example, binding of BAS is studied using various species of Bacillus mixed with unrelated proteins. Spore binding data may be analyzed with Hill plot analysis (see, e.g., Connors (1987) *Binding Constants: The Measurements of Molecular Complex Stability* (John Wiley & Sons, New York)).

EXAMPLE 8

Identification of Ligands

Ligands that bind to particular phage were identified using the approach developed recently for identification of phage-binding receptors on LnCAP cancer cells (Romanov et al. (2001) *Prostate* 47: 239-251). Phage that were affinity-selected to bind to prostate cancer cells were treated with a cross-linker to convert the phage into a water-soluble resin that was pelleted by low-speed centrifugation (Smith et al. (1998) *J. Immunol. Meth.* 215: 151-161). A sample known to contain the ligand was treated with NHS non-permeating biotinylating reagent (Pierce Biotechnology, Inc., Rockford, Ill.) to label the proteins in the sample. Cross-linked phage were incubated with the biotinylated sample and then precipitated along with bound labeled proteins. Proteins were eluted with mild acid, separated by SDS PAGE, transferred to a nitrocellulose membrane, labeled with streptavidin-peroxidase, and detected with an ECL detection kit (Amersham). Using this protocol, a 39 kiloDalton protein from prostate cancer cells was identified as binding to prostate cancer cell binding phage and is being sequenced. This identification of phage-binding ligands is important for rationalization of biosensor detection and also finds use in developing protective vaccines or drugs.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

While the preferred embodiments of the invention have been illustrated and described, it will be appreciated that various changes can be made therein without departing from the spirit and scope of the invention.

The invention claimed is:

1. A phage ligand sensor device comprising:

a) a sensor comprising a piezoelectric crystal; and b) a binding element comprising engineered phage, wherein said binding element is capable of binding to a ligand that is *Bacillus anthracis* bacteria or spores, wherein said phage have been engineered to express a foreign peptide known to bind to said *Bacillus anthracis* bacteria or spores, and wherein said foreign peptide comprises an amino acid sequence selected from the group consisting of DPRTVSTA (SEQ ID NO:8), DRTSSNTT (SEQ ID NO:9), DRSASSTA (SEQ ID NO:10), DRTSQNLQ (SEQ ID NO:11), DRSGTSPS (SEQ ID NO:12), DRNVNGPS (SEQ ID NO:13), ERGSNATL (SEQ ID NO:14), DSRNEKSM (SEQ ID NO: 15), ESRNSPAA (SEQ ID NO: 16).

2. The phage ligand sensor device of claim 1, wherein said binding element is coupled to said sensor by a layer of biotinylated lipid.

3. The phage ligand sensor device of claim 1, wherein said foreign peptide comprises an amino acid sequence of the β-galactosidase amino acid sequence.

* * * * *

UNITED STATES PATENT AND TRADEMARK OFFICE

CERTIFICATE OF CORRECTION

PATENT NO. : 7,267,993 B2
APPLICATION NO. : 10/289725
DATED : September 11, 2007
INVENTOR(S) : Petrenko et al.

It is certified that error appears in the above-identified patent and that said Letters Patent is hereby corrected as shown below:

On Title Page Item (75): “Valery A. Pentrenko” should read --Valery A. Petrenko--

Column 1

Line 15: “was supposed” should read --was supported--

Line 19: “matter or” should read --matter of--

Signed and Sealed this

Twenty Second Day of April, 2008

JON W. DUDAS
*Director of the United States Patent and Trademark Office*

SEQUENCE LISTING

<160> NUMBER OF SEQ ID NOS: 28

<210> SEQ ID NO 1
<211> LENGTH: 54
<212> TYPE: DNA
<213> ORGANISM: Artificial Sequence
<220> FEATURE:
<223> OTHER INFORMATION: degenerate coding sequence for the pVIII coat-protein gene
<220> FEATURE:
<221> NAME/KEY: misc_feature
<222> LOCATION: 5, 7, 8, 10, 11, 13, 14, 16, 17, 19, 20, 22, 23, 25, 26
<223> OTHER INFORMATION: n = A,T,C or G

<400> SEQUENCE: 1
gcagnknnkn nknnknnknn knnknnggat cccgcaaaag cggcctttga ctcc 54

<210> SEQ ID NO 2
<211> LENGTH: 18
<212> TYPE: PRT
<213> ORGANISM: Artificial Sequence
<220> FEATURE:
<223> OTHER INFORMATION: degenerate coding sequence for the pVIII coat-protein gene
<220> FEATURE:
<221> NAME/KEY: VARIANT
<222> LOCATION: 2, 3, 4, 5, 6, 7, 8, 9
<223> OTHER INFORMATION: Xaa = Any Amino Acid

<400> SEQUENCE: 2

```
Ala Xaa Xaa Xaa Xaa Xaa Xaa Xaa Xaa Asp Pro Ala Lys Ala Ala Phe
 1               5                  10                  15

Asp Ser
```

<210> SEQ ID NO 3
<211> LENGTH: 24
<212> TYPE: PRT
<213> ORGANISM: Artificial Sequence
<220> FEATURE:
<223> OTHER INFORMATION: Sequence Used to Generate f8-alpha Phage Library
<220> FEATURE:
<221> NAME/KEY: VARIANT
<222> LOCATION: 12, 13, 15, 16, 17, 19
<223> OTHER INFORMATION: Xaa = Any Amino Acid

<400> SEQUENCE: 3

```
Ala Glu Gly Glu Asp Pro Ala Lys Ala Ala Phe Xaa Xaa Leu Xaa Xaa
 1               5                  10                  15

Xaa Ala Xaa Glu Tyr Ile Gly Tyr
            20
```

<210> SEQ ID NO 4
<211> LENGTH: 8
<212> TYPE: PRT
<213> ORGANISM: Artificial Sequence
<220> FEATURE:
<223> OTHER INFORMATION: streptavidin binding motif
<220> FEATURE:
<221> NAME/KEY: VARIANT
<222> LOCATION: 3
<223> OTHER INFORMATION: Xaa = Glu or Asp
<220> FEATURE:
<221> NAME/KEY: VARIANT
<222> LOCATION: 4
<223> OTHER INFORMATION: Xaa = Gly or Ser
<220> FEATURE:
<221> NAME/KEY: VARIANT -continued
<222> LOCATION: 7, 8
<223> OTHER INFORMATION: Xaa = Any Amino Acid

<400> SEQUENCE: 4

Val Pro Xaa Xaa Ala Phe Xaa Xaa
 1               5

<210> SEQ ID NO 5
<211> LENGTH: 8
<212> TYPE: PRT
<213> ORGANISM: Artificial Sequence
<220> FEATURE:
<223> OTHER INFORMATION: neutravidin binding motif
<220> FEATURE:
<221> NAME/KEY: VARIANT
<222> LOCATION: 4
<223> OTHER INFORMATION: Xaa = Phe or Tyr
<220> FEATURE:
<221> NAME/KEY: VARIANT
<222> LOCATION: 5, 6, 7, 8
<223> OTHER INFORMATION: Xaa = Any Amino Acid

<400> SEQUENCE: 5

Val Pro Glu Xaa Xaa Xaa Xaa Xaa
 1               5

<210> SEQ ID NO 6
<211> LENGTH: 8
<212> TYPE: PRT
<213> ORGANISM: Artificial Sequence
<220> FEATURE:
<223> OTHER INFORMATION: beta-galactosidase consensus motif
<220> FEATURE:
<221> NAME/KEY: VARIANT
<222> LOCATION: 7
<223> OTHER INFORMATION: Xaa = Any Amino Acid

<400> SEQUENCE: 6

Glu Lys Thr Leu Ala Tyr Xaa Gln
 1               5

<210> SEQ ID NO 7
<211> LENGTH: 8
<212> TYPE: PRT
<213> ORGANISM: Artificial Sequence
<220> FEATURE:
<223> OTHER INFORMATION: beta-galactosidase consensus motif
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 5, 6, 7, 8
<223> OTHER INFORMATION: Xaa = Any Amino Acid

<400> SEQUENCE: 7

Xaa Thr Phe Ala Xaa Xaa Xaa Xaa
 1               5

<210> SEQ ID NO 8
<211> LENGTH: 8
<212> TYPE: PRT
<213> ORGANISM: Artificial Sequence
<220> FEATURE:
<223> OTHER INFORMATION: foreign peptide motifs selected by
      co-precipitation with spores

<400> SEQUENCE: 8

Asp Pro Arg Thr Val Ser Thr Ala

-continued 1 5

<210> SEQ ID NO 9
<211> LENGTH: 8
<212> TYPE: PRT
<213> ORGANISM: Artificial Sequence
<220> FEATURE:
<223> OTHER INFORMATION: foreign peptide motifs selected by co-precipitation with spores

<400> SEQUENCE: 9

Asp Arg Thr Ser Ser Asn Thr Thr
1 5

<210> SEQ ID NO 10
<211> LENGTH: 8
<212> TYPE: PRT
<213> ORGANISM: Artificial Sequence
<220> FEATURE:
<223> OTHER INFORMATION: foreign peptide motifs selected by co-precipitation with spores

<400> SEQUENCE: 10

Asp Arg Ser Ala Ser Ser Thr Ala
1 5

<210> SEQ ID NO 11
<211> LENGTH: 8
<212> TYPE: PRT
<213> ORGANISM: Artificial Sequence
<220> FEATURE:
<223> OTHER INFORMATION: foreign peptide motifs selected by co-precipitation with spores

<400> SEQUENCE: 11

Asp Arg Thr Ser Gln Asn Leu Gln
1 5

<210> SEQ ID NO 12
<211> LENGTH: 8
<212> TYPE: PRT
<213> ORGANISM: Artificial Sequence
<220> FEATURE:
<223> OTHER INFORMATION: foreign peptide motifs selected by co-precipitation with spores

<400> SEQUENCE: 12

Asp Arg Ser Gly Thr Ser Pro Ser
1 5

<210> SEQ ID NO 13
<211> LENGTH: 8
<212> TYPE: PRT
<213> ORGANISM: Artificial Sequence
<220> FEATURE:
<223> OTHER INFORMATION: foreign peptide motifs selected by co-precipitation with spores

<400> SEQUENCE: 13

Asp Arg Asn Val Asn Gly Pro Ser
1 5

<210> SEQ ID NO 14
<211> LENGTH: 8
<212> TYPE: PRT
<213> ORGANISM: Artificial Sequence
<220> FEATURE:
<223> OTHER INFORMATION: foreign peptide motifs selected by -continued

```
      co-precipitation with spores

<400> SEQUENCE: 14

Glu Arg Gly Ser Asn Ala Thr Leu
 1               5


<210> SEQ ID NO 15
<211> LENGTH: 8
<212> TYPE: PRT
<213> ORGANISM: Artificial Sequence
<220> FEATURE:
<223> OTHER INFORMATION: foreign peptide motifs selected by
      co-precipitation with spores

<400> SEQUENCE: 15

Asp Ser Arg Asn Glu Lys Ser Met
 1               5


<210> SEQ ID NO 16
<211> LENGTH: 8
<212> TYPE: PRT
<213> ORGANISM: Artificial Sequence
<220> FEATURE:
<223> OTHER INFORMATION: foreign peptide motifs selected by
      co-precipitation with spores

<400> SEQUENCE: 16

Glu Ser Arg Asn Ser Pro Ala Ala
 1               5


<210> SEQ ID NO 17
<211> LENGTH: 8
<212> TYPE: PRT
<213> ORGANISM: Artificial Sequence
<220> FEATURE:
<223> OTHER INFORMATION: foreign peptide motifs selected by
      co-precipitation with spores

<400> SEQUENCE: 17

Val Met Asp Arg Thr Gln Pro Pro
 1               5


<210> SEQ ID NO 18
<211> LENGTH: 8
<212> TYPE: PRT
<213> ORGANISM: Artificial Sequence
<220> FEATURE:
<223> OTHER INFORMATION: foreign peptide motifs selected by
      affinity-sorption to immobilized spores

<400> SEQUENCE: 18

Glu Pro Arg Ala Pro Ala Ser Leu
 1               5


<210> SEQ ID NO 19
<211> LENGTH: 8
<212> TYPE: PRT
<213> ORGANISM: Artificial Sequence
<220> FEATURE:
<223> OTHER INFORMATION: foreign peptide motifs selected by
      affinity-sorption to immobilized spores

<400> SEQUENCE: 19

Glu Pro Arg Leu Ser Pro His Ser
 1               5


<210> SEQ ID NO 20
```

-continued

<211> LENGTH: 8
<212> TYPE: PRT
<213> ORGANISM: Artificial Sequence
<220> FEATURE:
<223> OTHER INFORMATION: foreign peptide motifs selected by affinity-sorption to immobilized spores

<400> SEQUENCE: 20

Glu Pro Lys Pro His Thr Phe Ser
1 5

<210> SEQ ID NO 21
<211> LENGTH: 8
<212> TYPE: PRT
<213> ORGANISM: Artificial Sequence
<220> FEATURE:
<223> OTHER INFORMATION: foreign peptide motifs selected by affinity-sorption to immobilized spores

<400> SEQUENCE: 21

Glu Pro His Pro Lys Thr Ser Thr
1 5

<210> SEQ ID NO 22
<211> LENGTH: 8
<212> TYPE: PRT
<213> ORGANISM: Artificial Sequence
<220> FEATURE:
<223> OTHER INFORMATION: foreign peptide motifs selected by affinity-sorption to immobilized spores

<400> SEQUENCE: 22

Glu Thr Arg Val Pro His Gly Ala
1 5

<210> SEQ ID NO 23
<211> LENGTH: 8
<212> TYPE: PRT
<213> ORGANISM: Artificial Sequence
<220> FEATURE:
<223> OTHER INFORMATION: foreign peptide motifs selected by affinity-sorption to immobilized spores

<400> SEQUENCE: 23

Asp Ala Arg Gly Thr Thr His Met
1 5

<210> SEQ ID NO 24
<211> LENGTH: 8
<212> TYPE: PRT
<213> ORGANISM: Artificial Sequence
<220> FEATURE:
<223> OTHER INFORMATION: foreign peptide motifs selected by affinity-sorption to immobilized spores

<400> SEQUENCE: 24

Glu Lys Thr Pro Val Thr Ala Thr
1 5

<210> SEQ ID NO 25
<211> LENGTH: 8
<212> TYPE: PRT
<213> ORGANISM: Artificial Sequence
<220> FEATURE:
<223> OTHER INFORMATION: foreign peptide motifs selected by affinity-sorption to immobilized spores

<400> SEQUENCE: 25

-continued

```
Glu Arg Thr Val Ala Thr Thr Gln
 1               5


<210> SEQ ID NO 26
<211> LENGTH: 8
<212> TYPE: PRT
<213> ORGANISM: Artificial Sequence
<220> FEATURE:
<223> OTHER INFORMATION: foreign peptide motifs selected by
      affinity-sorption to immobilized spores

<400> SEQUENCE: 26

Val Thr Arg Asn Thr Ser Ala Ser
 1               5


<210> SEQ ID NO 27
<211> LENGTH: 8
<212> TYPE: PRT
<213> ORGANISM: Artificial Sequence
<220> FEATURE:
<223> OTHER INFORMATION: foreign peptide motifs selected by
      affinity-sorption to immobilized spores

<400> SEQUENCE: 27

Val Ser Gln Pro Ala Ser Pro Ser
 1               5


<210> SEQ ID NO 28
<211> LENGTH: 8
<212> TYPE: PRT
<213> ORGANISM: Artificial Sequence
<220> FEATURE:
<223> OTHER INFORMATION: foreign peptide motifs selected by
      affinity-sorption to immobilized spores

<400> SEQUENCE: 28

Glu Ser Phe Ser Ala Tyr Ser Gly
 1               5
```